US012007356B2

(12) United States Patent
Torsi et al.

(10) Patent No.: US 12,007,356 B2
(45) Date of Patent: Jun. 11, 2024

(54) FIELD EFFECT TRANSISTOR SENSOR AND A CORRESPONDING ARRAY DEVICE

(71) Applicant: UNIVERSITÀ DEGLI STUDI DI BARI ALDO MORO, Bari (IT)

(72) Inventors: Luisa Torsi, Bari (IT); Gaetano Scamarcio, Bari (IT); Eleonora Macchia, Bari (IT); Kyriaki Manoli, Bari (IT); Gerardo Palazzo, Bari (IT); Nicola Cioffi, Bari (IT); Rosaria Anna Picca, Bari (IT)

(73) Assignee: UNIVERSITÀ DEGLI STUDI DI BARI ALDO MORO, Bari (IT)

( * ) Notice: Subject to any disclaimer, the term of this patent is extended or adjusted under 35 U.S.C. 154(b) by 989 days.

(21) Appl. No.: 16/963,885

(22) PCT Filed: Jan. 26, 2018

(86) PCT No.: PCT/IB2018/050491
§ 371 (c)(1),
(2) Date: Jul. 22, 2020

(87) PCT Pub. No.: WO2019/145755
PCT Pub. Date: Aug. 1, 2019

(65) Prior Publication Data
US 2020/0348259 A1 Nov. 5, 2020

(51) Int. Cl.
*G01N 27/414* (2006.01)
*G01N 33/543* (2006.01)

(52) U.S. Cl.
CPC ..... *G01N 27/4148* (2013.01); *G01N 27/4145* (2013.01); *G01N 33/5438* (2013.01)

(58) Field of Classification Search
CPC ........... G01N 27/4148; G01N 27/4145; G01N 33/5438; H01L 29/786; H01L 29/06
USPC ......................................................... 257/253
See application file for complete search history.

(56) References Cited

U.S. PATENT DOCUMENTS

2007/0235760 A1* 10/2007 Shim ................. G01N 27/4145
257/192
2014/0264470 A1 9/2014 Fife et al.
2017/0131267 A1 5/2017 Lee et al.
2017/0350856 A1 12/2017 Kobayashi et al.

OTHER PUBLICATIONS

International Search Report and Written Opinion dated May 2, 2018. 15 pages.

* cited by examiner

*Primary Examiner* — Tu-Tu V Ho
(74) *Attorney, Agent, or Firm* — RMCK Law Group PLC

(57) ABSTRACT

A field effect transistor sensor includes: a source-drain channel, a semiconductor layer on said source-drain channel, a first gate electrode arranged above said semiconductor layer, a first well enclosing said source-drain channel, said semiconductor layer and said first gate electrode, the first well being configured to be filled, in use, with a first liquid, particularly a gating electrolyte, a second gate electrode arranged above the first gate electrode and exposed to an interior of the first well. Also disclosed is an array device including an array of field effect transistor sensors according to the above.

18 Claims, 18 Drawing Sheets

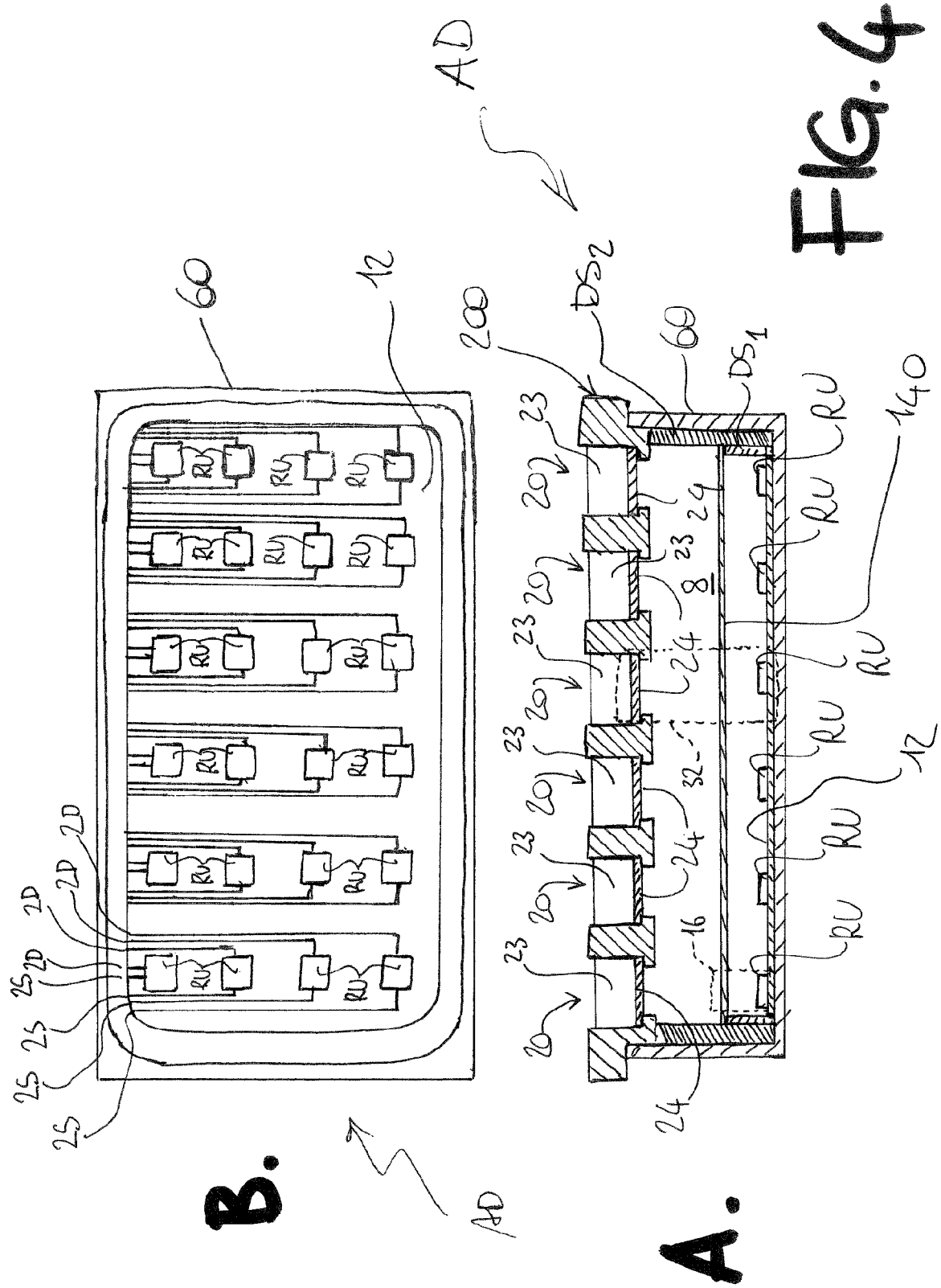

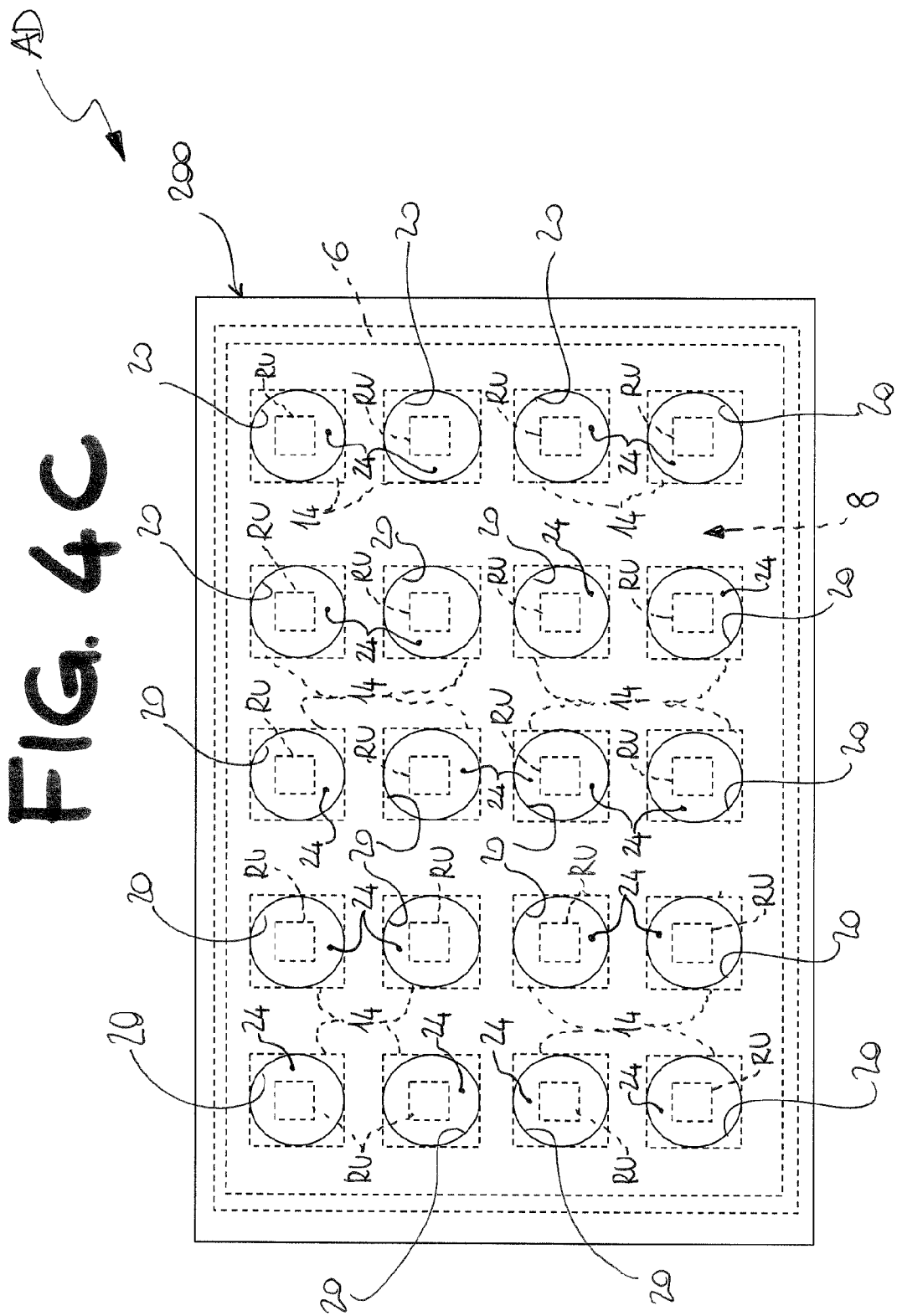

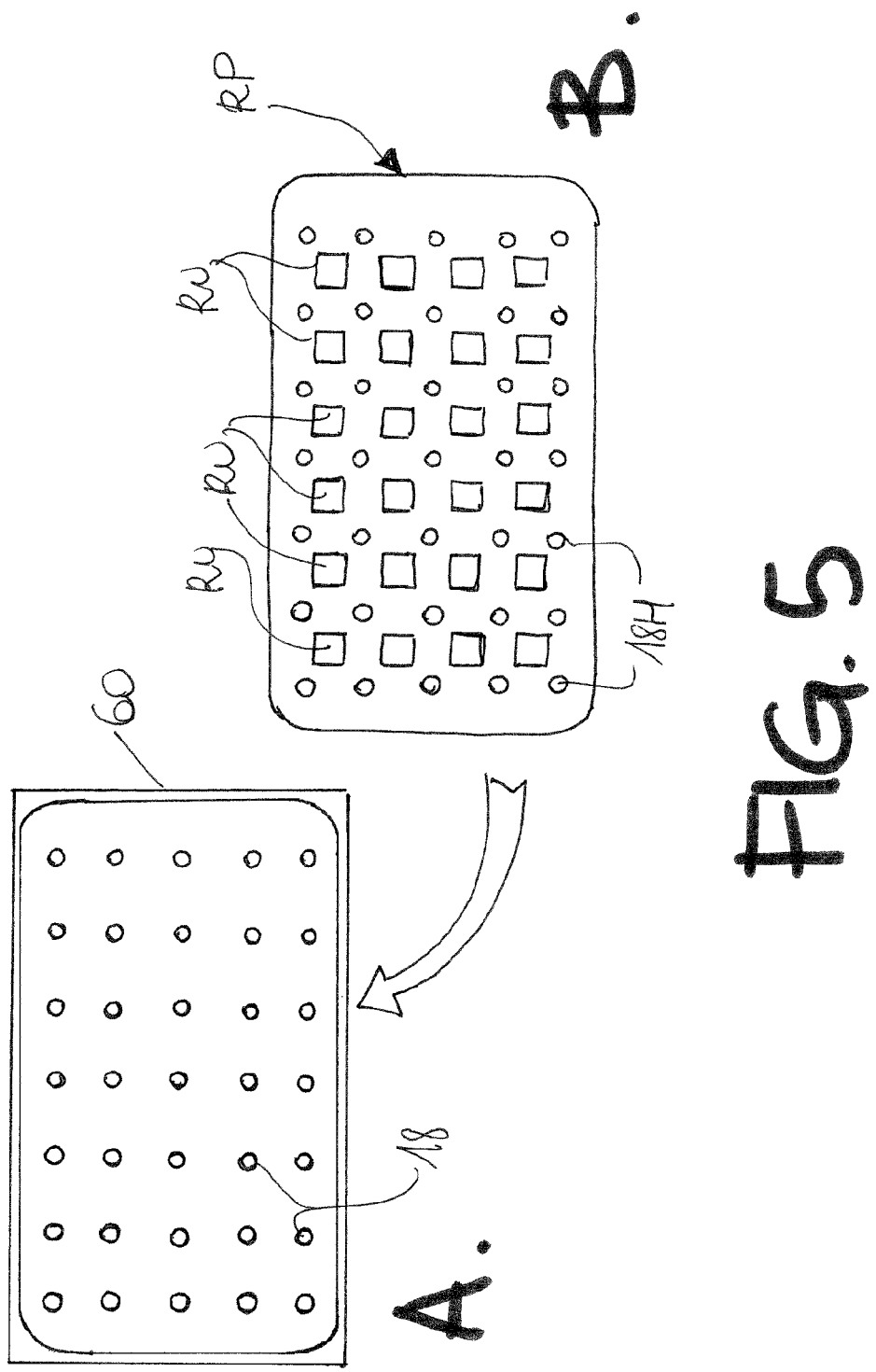

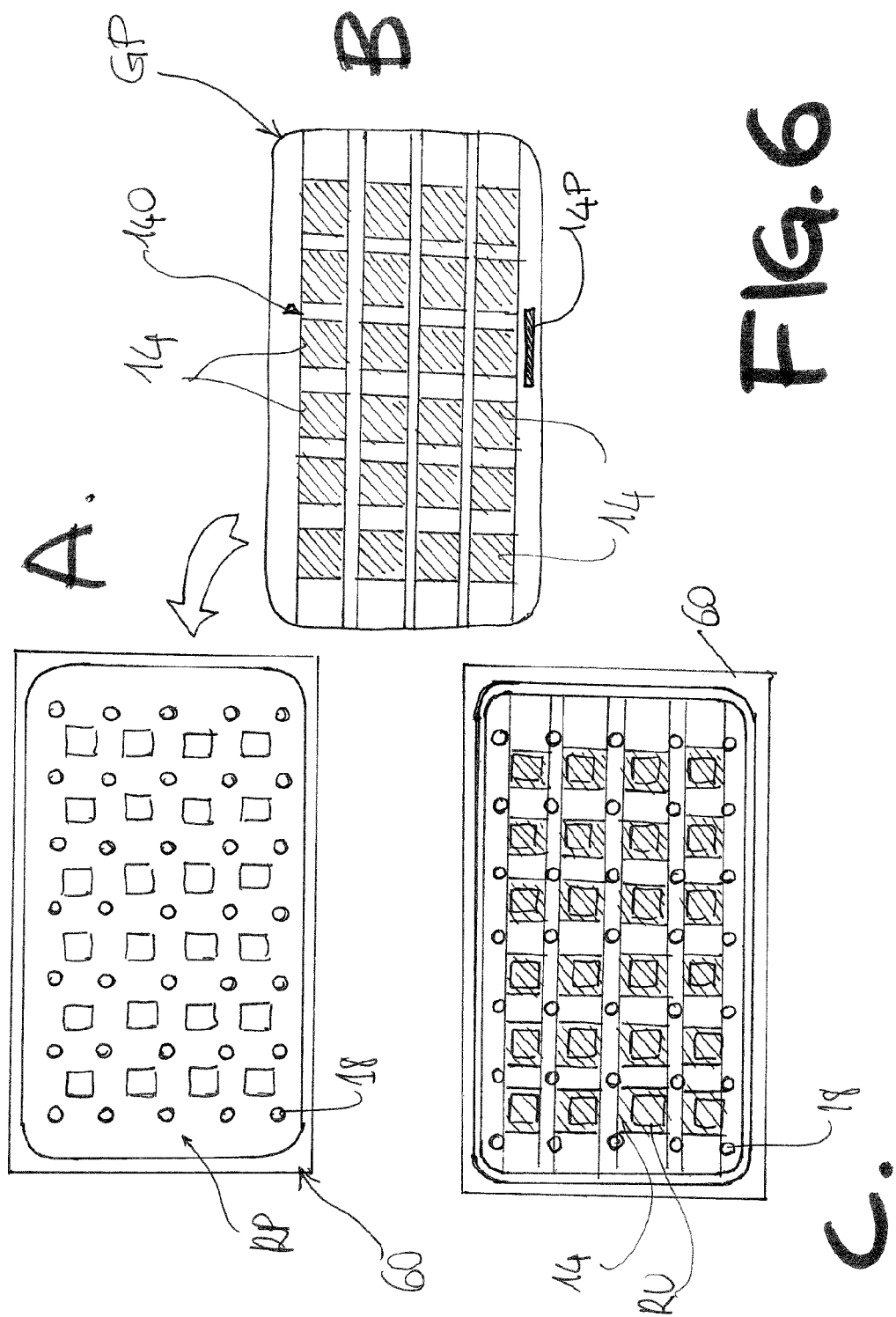

FIELD EFFECT TRANSISTOR SENSOR AND A CORRESPONDING ARRAY DEVICE

CROSS-REFERENCE TO RELATED APPLICATIONS

This application is a 371 National Stage of International Application No. PCT/IB2018/050491, filed Jan. 26, 2018. The disclosure of the above application is incorporated herein by reference in its entirety.

FIELD OF THE INVENTION

The present invention relates to field effect transistor sensors, particularly to field effect transistor sensors configured as biosensors.

PRIOR ART

In the field of biosensors, and particularly of field-effect transistor biosensors, the search for a sensing system capable of detecting biomarkers at the earliest possible stage of a disease development is gaining momentum as new technologies allow for more and more sensitive and reliable detection systems.

So far, however, the methodological approach has been driven by the idea that miniaturizing the sensing surface of a detector to the lowest possible size would be the way to proceed. Label-free single-molecule detection has been achieved via nano-systems that can incorporate or host, owing to size constraints, very few biological recognition elements.

To actually sense a single biomarker that is dispersed in a large volume of a biological fluid (i.e. a biomarker having an extremely low concentration), the binding events become so highly improbable that a nano-sensor would have to wait for an impractically long time to actually detect a few biomarkers. Accordingly, all of the above detection techniques are inherently unable to track few ligands in a biologically relevant medium as required for instance in biomarkers detection for early diagnosis, wherein the ligand concentration is extremely low in a bio-fluid.

Such nano-systems are also still limited by low reproducibility of the detection events (and the associated results) and production scalability, both being major issues in the transfer of a technological platform into real clinical applications.

Bioelectronics represents one of the most promising directions in printable or low cost production electronics and field effect transistors (FETs). Such devices, that can span dimensions from μm to mm in size, are based on materials such as printable organic semiconductors (OSCs). Among the others, organic FET, particularly electrolyte gated ones, have been demonstrated to work as highly performing bioelectronic FET (bio-FET) sensors.

While high sensitivity is assured by the FET transduction mechanism, selectivity is achieved by integrating a layer of functional biological recognition elements, directly coupled with an electronic interface. The study of such biological interfaces has provided insights into the conformational changes of the bio-systems serving as biological recognition element, upon direct interaction with the bio-marker to be detected, proving hence to be a label-free, sensitive and selective biosensing technology. FET-based sensors exhibit detection limits down to picomolar ($10^{-12}$ mole $L^{-1}$) and the high repeatability of the sensor responses is characterized by relative standard deviation as low as 3-5% for hundreds of repeated measurements. Up to $10^4$ repeated measurements in sea water were successfully performed with extremely high repeatability. Moreover, sub-femtomolar ($10^{-15}$ M, fM) detections were achieved with a graphene electrolyte-gated FET modified with human olfactory receptors 2AG1 (Park, S. J., Kwon, O. S., Lee, S. H., Song, H. S., Park, T. H. & Jang, J. Ultrasensitive Flexible Graphene Based Field-Effect Transistor (FET)-Type Bioelectronic Nose. Nano Letters 12, 5082-5090 (2012)). It is important to clarify that, taking into account the volumes of liquids typically analyzed with bio-FETs (100 μL), the number of detected ligands has been so far $10^8$ at pM concentration or $10^5$ at fM concentration, therefore the state-of-the-art in electronic label-free sensing is still very far from single-molecule detection.

The ability of an electrolyte gated FET constituted of a bio-interface that is populated by a large number of biological recognition elements to selectively detect affinity ligands (proteins and biomarkers in general) at the physical limit (e-Single-Molecule-Assay, e-SiMoA), is disclosed and discussed in EP application no. 16207596.4 in the name of the same Applicant.

A drawback of prior art biosensors constituted of a bio-interface that is populated by a large number of biological recognition elements, lies in the de-activation thereof following a single or very few ligand recognition events. In a prior art whenever a ligand recognition event occurs, the resulting local changes associated with a conformational variation, trigger collective phenomena that result in electrostatic and capacitive modifications in the packed receptors layer attached to the gate electrode. When the gate-filed is applied, such a change spreads very rapidly to the remaining of the biological recognition layer, thereby causing a signal amplification. This results in the biosensor being extremely sensitive but also rapidly becoming—so to say—"blind" to further ligand recognition events—possibly occurring at different ligand concentrations—as all of the remaining receptors on the gate electrode are deactivated. Such biosensors can in fact act as a sort of "binary" on-off response device, abruptly reaching saturation, to the presence of few ligands.

While such a phenomenon can enable the label-free detection of few proteins with a millimetre size device which is highly relevant per se, but it may prevent the biosensor from having a wide concentration dynamic range. A highly desirable feature would be that of keeping the single-molecule sensitivity of the biosensor but add to it also the ability to detect over a dynamic range at least three orders of magnitude.

These technical problems and the related solutions thereto are discussed in EP application 17177349.2 in the name of the same Applicant.

The inventors have notably observed that in addition to the drawbacks above, FET biosensors with the already patented layout and arrangement might still be subject to flaws such as instabilities and therefore detection performances lower than expectations and/or be inherently unsuitable for clustering in an array for use as an assay device.

OBJECT OF THE INVENTION

The object of the invention is that of overcoming the technical drawbacks of the prior art.

Specifically, the object of the invention is that of providing a field effect transistor sensor with better stability and hence detection performances, being mechanically and electrically stable, and being additionally suitable for clustering into an array that can be fabricated at low-cost for assay purposes.

SUMMARY OF THE INVENTION

The object of the invention is achieved by a field effect transistor sensor and an array device having the features of the appended claims, which form an integral part of the technical disclosure provided herein. More specifically, the object of the invention is achieved by a field effect transistor sensor including:
- a source-drain channel
- a semiconductor layer on said source-drain channel
- a first gate electrode arranged above said semiconductor layer,
- a first well enclosing said source-drain channel, said semiconductor layer and said first gate electrode, the first well being configured to be filled, in use, with a first liquid, particularly a gating electrolyte,
- a second gate electrode arranged above the first gate electrode and exposed to the interior of the first well.

The object is also achieved by an array device including an array of the above field effect transistor sensors.

BRIEF DESCRIPTION OF THE FIGURES

The invention will now be described with reference to the attached figures, provided purely by way of non limiting example, and wherein FIG. 4A is a schematic sectional view of an array device according to an embodiment of the invention, while FIG. 4B is a plan view thereof with some components removed, and FIG. 4C is a plan view of the full array device, FIGS. 5 and 6 schematically show an assembly sequence of a lower portion of the device of FIGS. 4A and 4B, with added pillar elements FIG. 7 schematically show an assembly sequence of an upper portion of an embodiment of the device of FIGS. 4A and 4B, FIG. 8 shows a FET biosensor according to another embodiment of the invention, while

DETAILED DESCRIPTION OF PREFERRED EMBODIMENTS

Figure 1:
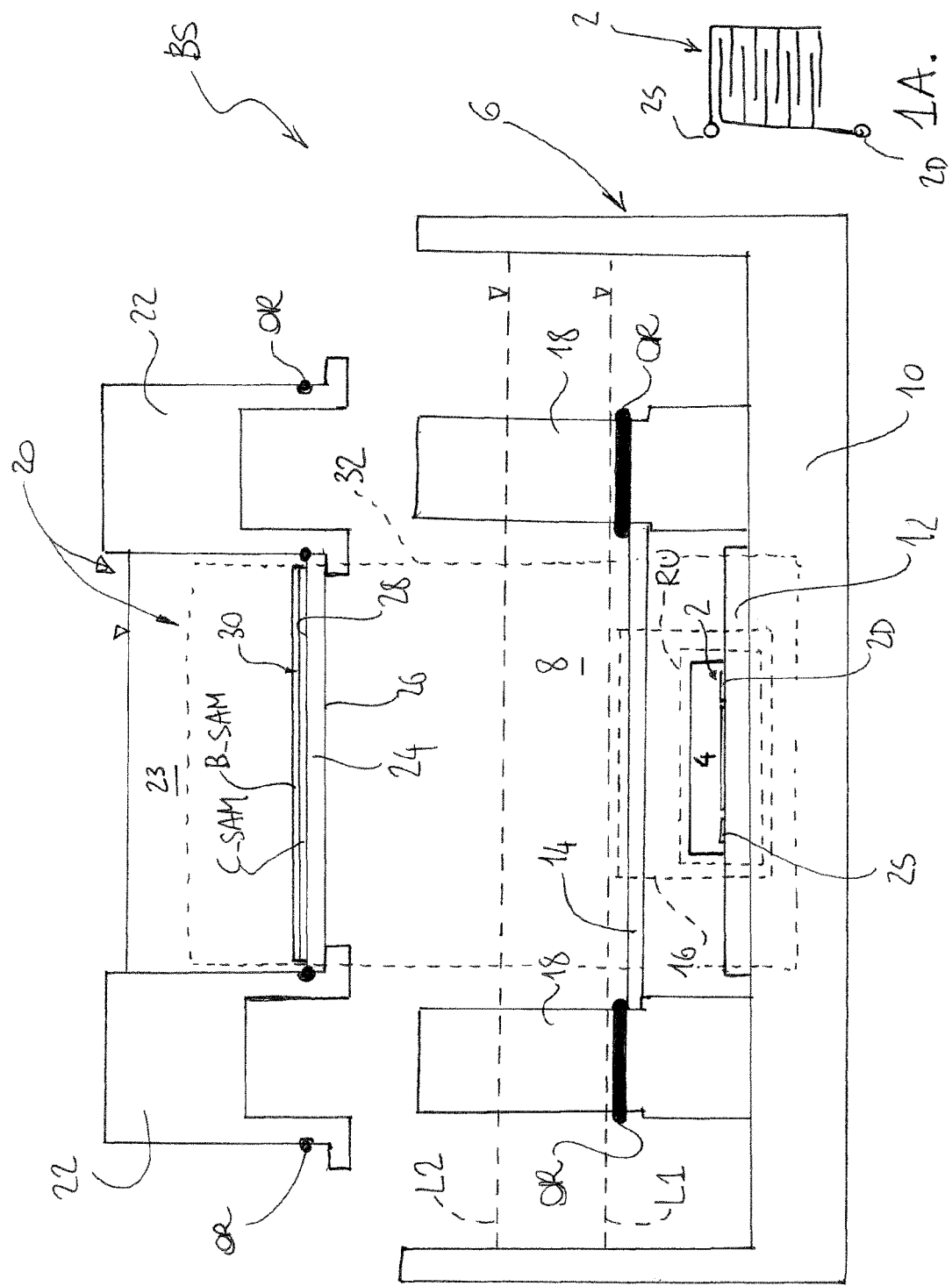
FIG. 1 is a schematic exploded view of a FET biosensor according to an embodiment of the invention.

Reference BS in FIG. 1 designates as a whole a field effect transistor sensor (also referred to herein as "biosensor" or bio-FET or bio-TFT) according to a first embodiment of the invention. The biosensor BS includes a source and drain channel 2 and a semiconductor layer 4 on said source and drain channel 2. The source and drain channel 2 includes source (S) and drain (D) electrodes, preferably provided as gold contact pads made by UV (photo)lithography and designated, respectively, by reference numbers 2S, 2D. Throughout the description, the source and drain electrodes may be referred to as "source pad" and "drain pad" respectively, whether or not in association to the respective reference numbers 2S and 2D.

The source and drain pads are connected to an interdigitated pattern of gold electrodes that defines the FET channel, a schematic representation of which is provided in FIG. 1A. In a preferred embodiment, the interdigitated pattern (FET channel) is 1280 μm wide (W, equipotential electrode region) and 5 μm long (L, distance separating two differently biased regions) so as the overall are is 0.06 cm$^2$. They can be defined by electron-beam deposited gold (50 nm thick) and a prior deposited layer of titanium (5 nm thick) serving as adhesion layer. The area separating two differently biased regions L may be as large as 5-200 μm, and can be used with the width W scaled proportionally, or with less fingers and channels if the size of the overall pattern becomes larger than the gate area. L spacing larger than 100 μm, can also be considered to enable the printing or the definition through screen mask of the interdigitated pattern. In the description that follows, such interdigitated pattern will be oftentimes referred to as "interdigitated S and D pattern". Different S and D geometrical patterns—both interdigitated or not—can be used. A simpler geometry of S and D pads can be that of two rectangles that are separated in their longer dimension, that is W, by a distance L.

In the preferred embodiment, source (S) and drain (D) pads (and the interdigitated electrodes) are defined by UV photolithography and electron-beam evaporated gold (50 nm thick) and a prior deposited layer of titanium (5 nm thick) serving as an adhesion layer. Alternatively, these pads can be defined by screen printing of a conducting ink or by means of thermal or e-beam evaporation of titanium first and gold afterwards trough a shadow mask.

The source pad and the drain pad are covered and connected at the source and drain channel by means of the semiconductor layer 4. While this is the preferred embodiment, alternatively, the source and the drain pads can be deposited, by printing for instance, on top of the semiconductor layer 4. The combination including the source and drain channel (as well as the source and drain pads) and the semiconductor 4 is generally known as "resistor unit" RU and as such will be addressed in the following description.

A first well 6—or, as will become apparent in the following—lower well—encloses the source and drain channel 2, the source and drain pads 2S, 2D, and the semiconductor layer 4 (hence it encloses the resistor unit RU). The well 6 is filled in use with a first liquid 8, namely a gating electrolyte, preferably HPLC-grade water or low ionic-strength electrolytes.

HPLC-grade water is obtained by filtering through mixed bed deionization and with 0.2 μm membrane filters. The typical specifications for such water are: resistivity>18 megaohms (mΩ) at 250 C; total organic carbon<5 ppb; Silica<3 ppb; Sodium<1 ppb; Chloride<1 ppb; no bacteria.

The well 6 is preferably made of plastic material (e.g. polystyrene) and comprises a bottom 10 whereon a substrate 12 arranged (and attached) carrying the resistor unit. Specifically, the source and drain pads and the source and drain channel are deposited onto the substrate 12, while in the preferred embodiment, the semiconductor layer 4 is deposited onto the source and drain channel.

The substrate 12 can be made out of flexible or rigid plastic as well as of glass or Si/SiO$_2$. Alternatively a glass slide or a flexible plastic substrate such as polyimide (Kapton®), mica (phyllosilicate, exhibiting a two-dimensional sheet or layer structure), poly(ethylene 2,6-naphthalate) or polyethylene terephthalate can be used. Event textile such as for instance silk based ones (that are also a biocompatible material) can be used as substrates.

The semiconductor 4, forming the FET channel layer, can be made out of p-type or n-type organic or inorganic material, and specifically of a printable e non printable organic material such as (P3HT, poly(3,4-ethylenedioxy-thiophene): poly(styrenesulfonate (PEDOT-PSS), PBTTT-Cx, poly[9,9-dioctylfluorene-co-bithiophene] (F8T2), 6,13-bis (triisopropylsilylethynyl) TIPS pentacene, polyquaterthiophenes (PQTs), benzobis(thiadiazole) (BBT), 1,4,5,8-naphthalene-tetracarboxylic dianhydride (NTCDA), just to quote a few. Inorganic materials such as binary oxides ($ZnO$, $In_2O_3$, $SnO_2$, $Ga_2O_3$), ternary oxides (ZIO, ITO, ZTO, IGO) and quaternary compounds (IZTO, IGZO), chalcogenides (cadmium sulfide (CdS), cadmium selenide (CdSe). Moreover, carbon nanotubes or nanowires as well as water stable 2D materials such as graphene, phosphorene, black phosphorous, molybdenum disulfide or molybdenum trioxide, can also be used as a material for the semiconductor 4. This is an incomplete and non-exhaustive list of possible semiconductors that can be used as channel materials 4.

In a preferred embodiment, the semiconductor 4 is made of hydrophobic poly(3-hexylthiophene-2,5-diyl)—or P3HT—exhibiting the following properties: regioregularity>99%, average molecular weight of 17.5 kDa g mol$^{-1}$. A P3HT solution (2.6 mg ml$^{-1}$ in chlorobenzene) filtered with a 0.2 µm filter was spin-coated at 2.000 r.p.m. for 20 s and annealed at 80° C. for 1 (one) hour. In the preferred embodiment, the total semiconductor area is 6.5 10$^{-3}$ cm$^{-2}$. The P3HT surface is highly hydrophobic as the contact angle is as large as 103±3°.

Alternatively, poly[2,5-bis(3-tetradecylthiophen-2-yl) thieno[3,2-b]thiophene](PBTTT-C14), poly(2,5-bis(3-hexadecylth-iophene-2-yl)thieno[3,2-b]thiophene (pBTTT-C16), pBTTT-C14 as well as solution processed pentacene. Specifically, PBTTT-C14 can be dissolved (7 mg/ml) in a mixture of 1,2-dichlorobenzene and chloroform (in 9:1 ratio). PBTTT-C14 solution can be spin deposited at 7,000 r.p.m. for 60 s and annealed at 120° C. for 10 min.

Yet preferably, the semiconductor layer 4 can be formed by a nanostructured material comprising a p-type semiconductor such as for instance Poly(3-hexylthiophene-2,5-diyl) (P3HT) added with zinc-oxides (ZnO) nanoparticles that are n-type. Other p-type organic semiconductor could be poly (3,4-ethylenedioxythiophene), poly(styrenesulfonate (PEDOT-PSS), PBTTT-Cx, poly[9,9-dioctylfluorene-co-bithiophene] (F8T2), 6,13-bis (triisopropylsilylethynyl) TIPS pentacene, polyquaterthiophenes (PQTs), benzobis(thiadiazole) (BBT), just to quote a few while the n-type nano-sized elements can be nanoparticles, nanowires, nanorods, nanotubes of $In_2O_3$, $SnO_2$, CdSe, fullerene-like nanoparticles or nano-rods of $WS_2$, and similar selenides, or fullerene ($C_{60}$). At the same time, an n-type semiconductor hosting p-type nano-structured elements can be envisaged too The details of the P3HT+ZnO-NP layer 4 preparation are as follows: ZnO nanoparticles (ZnO-NPs) are preferably prepared by a two-step procedure. First, electrochemical synthesis is performed with a three-electrode cell.

To this end two twin zinc sheets (as anode and cathode, purity 99.99%) and an Ag/AgCl (KCl sat.) electrochemical reference electrode are used. Zinc electrodes were polished using sandpaper, and afterwards, using alumina powder. Then, they undergo three cycles of ultrasonic cleaning alternating Milli-Q water and 2-propanol. Each steps last 10 minutes. The electrodes are then activated in 1 M HCl for 30 s just before use. The electrosynthesis is carried out at constant current density j=10 mA/cm$^2$ for 1 h, under stirring at room temperature.

The electrolytic medium consists in a 30 mM $NaHCO_3$ aqueous solution with 1 g/L poly(sodium 4-styrenesulfonate) (PSS, average Mw~70,000, powder). Afterwards, the colloidal dispersion is centrifuged at 5000 rpm for 45 minutes. The resulting precipitate is dried overnight at 70° C., and then calcined at 600° C. for 1 h. Spheroidal particles with size 50±10 nm are eventually obtained. Alternatively, ZnO-NPs (and other nanostructured n-type inorganic semiconductors) can be prepared by hydrothermal or sol-gel methods starting from precursor salts.

The nanocomposite is prepared by adding the ZnO-NPs to the P3HT solution. P3HT, regioregular, electronic grade, 99.995% trace metal basis, Mw~15.000-45.000, is first dissolved in chlorobenzene in concentration 2.6 mg/mL and put under sonication for 30 minutes. Then, the solution is filtrated on 0.2 µm PTFE filters. Afterwards, the ZnO-NPs are added to the filtrated P3HT solution in concentration of 1.5 mg/mL. The suspension is sonicated for 40 minutes for complete mixing. The P3HT+ZnO-NP layer 4 was spin-coated at $2\times10^3$ r.p.m. for 20 s and annealed at 80° C. for 1 hour.

A first gate electrode 14 is arranged above the semiconductor layer 4 (hence above the resistor unit RU) and spaced therefrom by a fixed distance. The gate electrode 14 is an electronic-reference-gate electrode and is enclosed into the well 6 and in use is completely immersed into the first electrolyte filling the volume thereof. The gate electrode 14 has preferably a squared shape and has an area of 0.001-1 cm$^2$, preferably 0.6 cm$^2$. It is made out of a bulk noble metal such as gold, so that all the surfaces thereof are equipotential. The gate can be made of a rigid material so as to resist buckling or bending, and, once stability secured in its position, to provide mechanical and electrical stability.

To this end it can be made out also of a rigid bulk gold lamina, or it may comprise a rigid core made of plastic or of a metal that is less noble than gold such as Cu, Ag, brass etc. which is pleated or covered by a gold layer. The gate electrode 14 may also be manufactured according to either of the techniques shown in FIGS. 7A to 7F, or FIGS. 7G to 7J, or else 7K to 7L.

A millimeter-sized clamp can also be used at one end of the plated gate electrode with an insulating core, to short-circuit the two layers of gold deposited on the two larger surfaces of 14 so as both surfaces in contact with the water electrolyte 8 are equipotential.

Note that the semiconductor layer 4 becomes a field-effect-transistor (FET) or a thin-film-transistor (TFT) channel when a gating system is capacity coupled to it. The gating system in this case comprises an ionic-conductive and electronic-insulating (ICEI) water layer corresponding to the electrolyte in the well 6, and the electronic-reference-gate electrode 14. This is schematically identified in the figures a water-gated TFT 16.

One or more resistor units RU can be clustered and associated to a single electronic-reference-gate electrode 14. Preferably, 1 to 10 separate (and separately electrically addressable) resistor units RU can be associated to a single gate 14. To this end, the gate 14 preferably has a surface area ranging from 1 to 1,000 times the area of the interdigitated S and D pattern so as to address each RU. In a preferred embodiment the gate 14 area is 100 times that of the single or clustered RUs although it can be demonstrated that, as long as the area of electronic-reference gate 14 is larger than a single RU or of the whole area of the cluster of RUs, it will function properly.

The electronic-reference-gate electrode 14 is spaced from the resistor unit either by way of a circular or quadrangular rim—either a separate item or being part of the sidewall of the well 6. Alternatively, the electronic-reference-gate electrode 14 can be supported by means of a plurality of pillars 18 protruding from the bottom 10 of the well 6, and preferably made integrally with the well bottom. The pillars 14 are preferably arranged according to a quadrangular mesh, but in case of a circular gate electrode 14 they can be arranged according to a triangular or otherwise polygonal mesh. The quadrangular—particularly square—mesh is anyway a preferred option.

Figure 2:
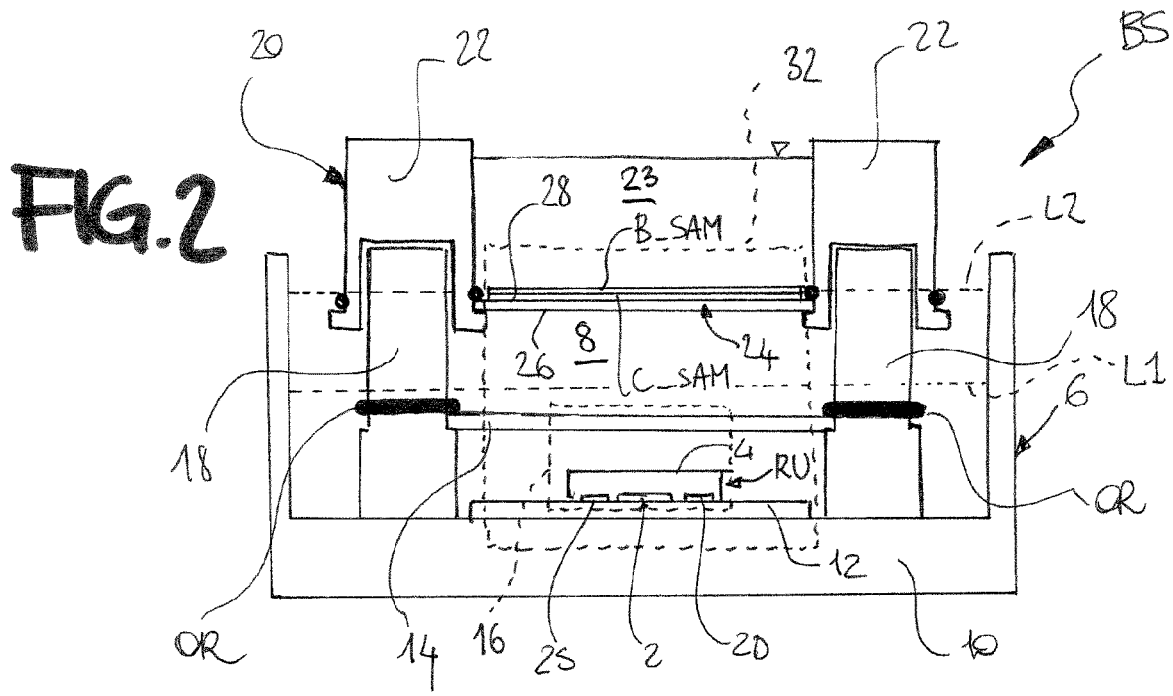
FIG. 2 is an assembled view corresponding to FIG. 1.

As visible in FIGS. 1, 2, the gate 14 is held at a fixed distance (height) from (and above) the resistor unit RU by sitting the same on shoulders or grooves provided in each of the pillars 18 of a mesh surrounding the resistor unit (or the set of resistor units).

The mechanical stability of the structure is improved by securing the gate in such seats by means e.g. of o-rings OR, or alternatively by means of washers fitted onto the pillars 18. In case the gate electrode 18 is supported by a peripheral rim, a locking ring can be used on the inside diameter of the rim.

The distance between the resistor unit and the electronic-reference-gate 14 of the water-gated TFT 16 is therefore fixed. Such a structure enables the measurement of the source-drain current of the TFT 16 and hence of the current induced in the TFT channel, by polarizing the electronic-reference-gate 14 held at a fixed position at all times. This will enable to keep current changes in the TFT channel due to spurious process such as the channel material degradation, under control at all time. The gate 14 can also be used to stabilize the semiconductor 4 prior to begin the sensing measurements.

Not only do the pillars 18 act as spacers for the gate electrode 14, they are also configured to support a second well 20 which is above and stacked onto the first well 6. The second well 20 is essentially arranged as a lid covering the first well 6, so that overall the biosensor BS includes a lower well 6 covered by an upper well 20 as lid.

The second well 20 is coupled to cups 22 which are configured to fit onto the pillars 18 to mate the well 20 to the well 6. Alternatively, the well 20 may rest on a peripheral rim provided at the upper edge of the sidewall of the well 6, in which case the cups 22 are replaced by a single flange going all around the well 20.

The bottom of the second well 20 is provided at least partly, and preferably as a whole, by a second gate electrode 24 which is a sensing-gate electrode. The electrode gate 24 is therefore arranged above and at a distance from the electronic-reference gate electrode 14. The sensing-gate electrode 24 is—similarly to the gate 14—a square or, preferably, a circular lamina made of gold or having a gold layer covering the whole surface thereof. The gate sensing-electrode 24 has an area ranging from 1 to 1,000 times that of the RU surface, so it can range from 0.001-1 $cm^2$. Preferably, the sensing-gate 24 is at least 10 times larger than the single or clustered RU units to which it is coupled. In the most preferred embodiment it has an area in the 0.2-0.8 $cm^2$.

It includes opposite faces, namely a first face 26 exposed to the interior of the first well 6, and a second face 28 facing the interior of the well 20, which in use is filled with a second liquid 23. More specifically, the gate 24 being the sensing-gate, and as such the second face 28 is coated with a layer of biological recognition elements designated by the reference 30, which comprises one or more specific binding pair forming substances.

Alternatively, the second well 20 can be a separate body put at the side of the lower and main well 6. In this configuration, well 20, is made out completely of plastic and serves to contain all the solutions needed to functionalize the sensing-gate 24 as well as the standard solutions and the sample to be analysed. Hence in such a case, the sensing-gate 24 is not integrated into well 20, but is immersed directly into well 6 on top of the electronic-reference gate 14 and at a given distance from it. The sensing-gate in this configuration is a rectangular rigid gold lamina that is L-shaped so as the squared horizontal 'feet' of the "L" (0.8×0.5 $cm^2$ wide 0.3 mm thick) is the actual gate area, while the vertical "leg" of the "L" enables the contact to be taken directly by a probe.

Figure 3:
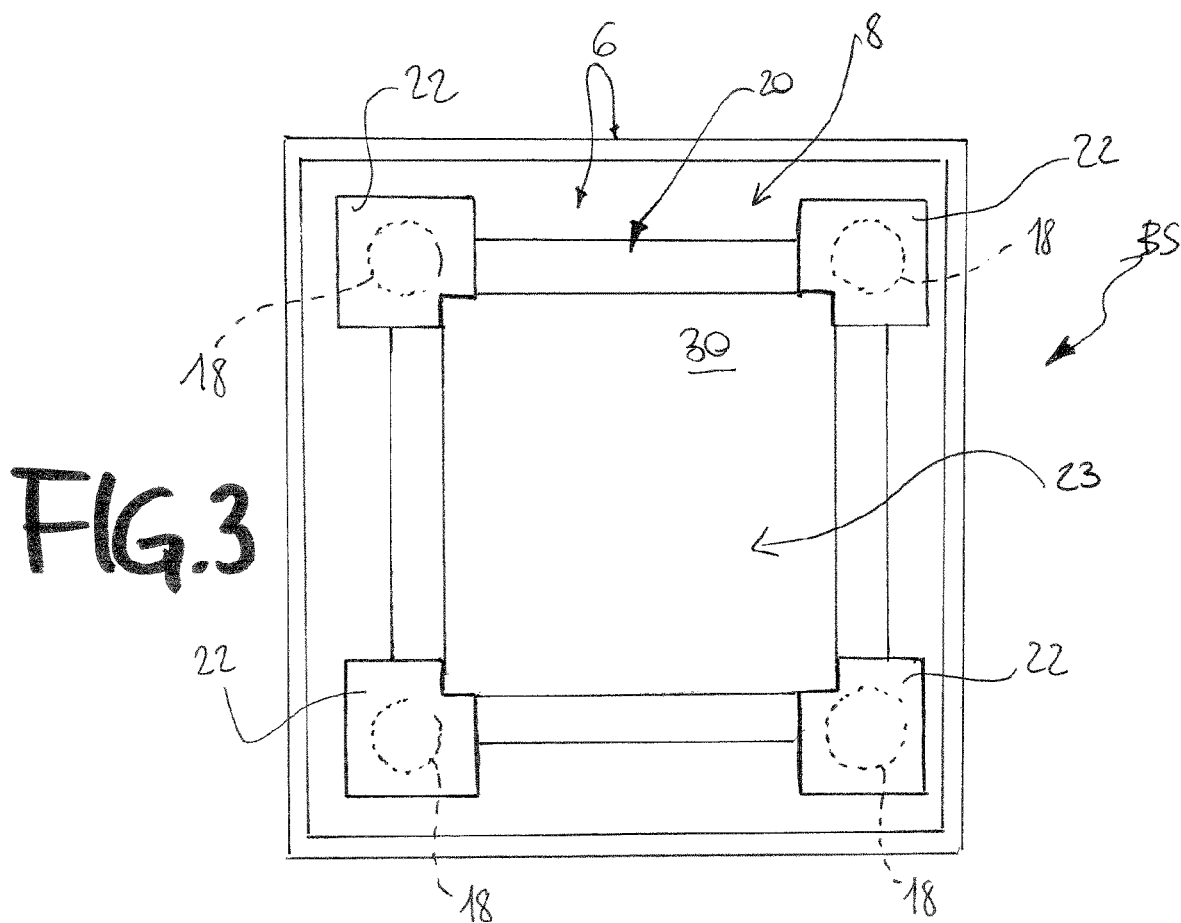
FIG. 3 is a plan view of the biosensor of FIGS. 1 and 2.

Going back to the structure of the stacked wells in FIG. 1 and FIG. 2, namely the sensing system with the second (upper) well 20 positioned on the first (lower) well 6, shown in FIGS. 2 and 3, here, the well 20 is also detailed showing both a schematic of the cross-section (FIG. 2) and the top-view (FIG. 3). As it can be seen in the cross-section the second well 20 is stacked onto the first well 6 (here by positioning over the pillars 18), so that the gate 24 is exposed to the first well 6. In use, when the first well 6 is filled with the first liquid 8 (HPLC water as gating electrolyte or other electrolytes), the gate electrode 24, and particularly the surface 26 thereof, is in contact (or more generally simply exposed, see below) with the liquid 8 in the well 6, while the layer of biological recognition elements 30 on the second face 28 is exposed the well 20, ready to come into contact with the second liquid 23 that is poured therein. The water-gated TFT that is gated by the sensing-gate 24 is addressed as 32 and is provided by the TFT-channel or equivalently by the resistor unit (RU) that is capacitive coupled to gate 24 by means of the liquid 8 and also liquid 23. When the TFT is in operation both liquids 8 and 23 are made of HPLC water.

As shown in FIG. 1, the well 6 can be filled with water 8 at two different levels, namely a higher level L2 which provides for a coupling between the TFT 16 and gate 24, and a lower level L1 to be resorted to in case the TFT 16 needs to be totally decoupled from gate 24.

The well 20 is configured to receive the second liquid 23, that can be the liquids to bio-functionalize the sensing-gate 24 as well as—in use—the bio-fluids to be analyzed or the HPLC-water used during the sensing measurements.

The layer of biological recognition elements 30 includes self-assembled monolayers (SAMs), more specifically a chemical self-assembled monolayer (chemical SAM or C_SAM) provided on the surface of the side 28, and a biological self-assembled monolayer (biological SAM or B_SAM) provided over the chemical SAM, which essentially acts as an attachment interface to the gate electrode 24. In certain embodiments, the chemical SAM may be dispensed with (see the following description) and the biological SAM may be treated to exhibit grafting properties to the gold surface of the gate 24.

The bio-functionalization process is performed with one of methods that will be described in the following paragraphs. The well 20, that surrounds the gate area with its walls, can be used to bio-functionalize the gate by pouring in the well all the required solutions for each chemical (C_SAM) or bio-functionalization (B_SAM) step. Between each functionalization step the well 20 is emptied by pipetting the solution away (or removing the solution with other means) and are washed thoroughly with HPLC-grade water afterwards. So as, also the cleaning steps are accomplished, when necessary, using well 20.

The surface of the side 28 is bio-functionalized by forming the layer of biological recognition elements thereon. Said layer of biological recognition elements 30 includes one of:
- a complex of a chemical self-assembled structure and a biological self-assembled structure of one or more specific-binding-pair-forming substances, wherein the biological self-assembled structure is chemically grafted onto the chemical self-assembled structure, or
- a biological self-assembled structure of one or more specific-binding-pair-forming substances, wherein the structural units of the biological self-assembled structure are treated to exhibit grafting properties in respect of the substrate they are intended to graft on i.e. the gold surface of the sensing-gate electrode 24.

The specific-binding-pair-forming substances can be attached to the gold surface 28 also by using an anchoring protein such as streptavidin, but also avidin or neutravidin. These biotin-binding proteins can be physically adsorbed to the gold, or can be attached to a chemical SAM. A biotinylated specific-binding-pair-forming substances is attached to the streptavidin as well as to avidin in such a case. A G-protein can also serve as specific-binding-pair-forming substances anchoring system. Both these methods will allow to better orientate the specific-binding-pair-forming substances when attached to the gate surface. For more details, see FIG. 2 in Manoli et al. Angewandte Chemie Volume 54, Issue 43, Oct. 19, 2015 Pages 12562-12576.

In the preferred embodiment, the layer of biological recognition elements 30 includes however a chemical self-assembled monolayer (C_SAM in the figures) and a biological self-assembled monolayer (B_SAM in the figures) of one or more specific-binding-pair-forming substances. In the array configuration each sensing-gate 24 will be functionalized with a different biological-recognition element to enable multiplexing functions, that is to say it will enable simultaneous measurement of multiple analytes (dozens or more) in a single run/cycle of the assay. It is distinguished from procedures that measure one analyte at a time.

In the array configuration, each different biological-recognition element on a given gate 24 will enable the specific detection of a bio-marker as the former is to be chosen so as the biomarker is its affinity ligand or more generally is the biological species with which the biological-recognition element forms a stable complex on the gate 24 surface. Yet further, in another preferred embodiment the layer of biological recognition elements is patterned into a plurality of uncoupled domains as disclosed in EP application no. 17177349.2 in the name of the same Applicant.

While the C_SAM options have been detailed in EP application no. 17177349.2 and no. 16207596.4, according to the invention, said one or more specific-binding-pair-forming substances include one or more of the following:
- antibodies or antigens (one or more) against a selected bio-marker,
- antibodies or antigens Fab fragments,
- anti-human Immunoglobulin (anti-hIG) antibodies,
- anti-human Immunoglobulin G (anti-IgG) antibodies,
- anti-human Immunoglobulin M (anti-IgM) antibodies,
- anti-C Reactive protein (anti-CRP),
- anti-troponin,
- peptides
- specific-binding-pair-forming substances for a given antibody or antigen, dopamine, chiral odors, DNA, PNA, peptides, exosomes, polypeptides, human glycoprotein, inflammatory cytokines, C-reactive proteins, viruses.

In embodiments only featuring a biological self-assembled structure, the same is a self-assembled monolayer of one or more specific-binding-pair-forming substances with a thiol group able to spontaneously attach to the gold surface such as, but not limited to, proteins modified in such a way as to have an exposed cysteine. Direct physical adsorption of capturing proteins or of specific-binding-pair-forming substances is also considered. Namely, the specific-binding-pair-forming substances are let to directly attach (physical adsorption) to the gold surface (cleaned as specified in the following) without the presence of any type of purposely attached C_SAM.

In the preferred embodiment, the gate electrode functionalization method provides that a SAM layer B_SAM of anti-human Immunoglobulin G (anti-IgG, preferred), anti-human Immunoglobulin M (anti-IgM), anti-C Reactive protein (anti-CRP) or anti-troponin, antibodies, anti-exosomes or peptides be added covering the whole gate surface, and specifically be grafted onto a C_SAM layer grafted to the surface 28 of the gate electrode 24 to be functionalized. Clearly, the invention can be practiced with other specific-binding-pair-forming substances (e.g. a selected antibody for a target biomarker) such as for instance those to selectively recognize the biomarkers for tumors of all kinds or neurodegenerative as well as other progressive diseases.

Indeed, the platform herein proposed is conceived as a general purpose ultra-sensitive detection tool that can be specified to be selective for a given biomarker as long as the relevant specific-binding-pair-forming substances is available. Moreover, an array of 2 to 100 biosensor systems as the one described in FIGS. 4 and 5, featuring 20 bio-sensor, can be realized to endow the invention with multiplexing properties so as contemporarily quantify a number of biomarkers known to be needed for the diagnosis of a given disease or for the assessment of its progression. In this configuration each sensing-gate in a given well (or a whole row of them to gather results in replicates and/or to build the calibration curve) will be bio-functionalized with a different biological-recognition element to capture one of the biomarkers to be analysed.

The procedures used to attach the biological-recognition elements to the C_SAM to form the B_SAM are general as involve reactions with the exposed amino or carboxyl groups (depending on the chosen activation chemistry) that are ubiquitary to all the proteins and also to peptides that are characteristics solely of the antibodies or other specific-binding-pair-forming substances. This renders the deposition method extendable i.e. to all of the biological species mentioned above (all the antibodies or antigens, DNA, PNA, human glycoprotein, or receptors for dopamine, chiral odors, inflammatory cytokines, C-reactive proteins, peptides, exosomes, troponin). This is therefore an essentially general platform for immunoassay and for bioassay in general.

The one or more specific-binding-pair-forming substances (such as for instance anti-hIg, anti-IgG, anti-IgM, anti-CRP, anti-troponin but also antibodies in general as well as peptides) immobilized in the layer of biological recognition elements 30 (particularly in the B_SAM) are packed at a density comprised between $0.1 \times 10^4$ $\mu m^{-2}$ and $10 \times 10^4$ $\mu m^{-2}$ depending on the size of the biological species that is attached to the electrode. In case of an anti-IgG antibody it is preferably between $1 \times 10^4$ $\mu m^{-2}$ and $2 \times 10^4$ $\mu m^{-2}$.

In the preferred embodiment, the C_SAM on the surface 28 of the gate electrode 24 is produced by first cleaning the gold free-standing platelet (sensing-gate electrode 24) as follows:

first, the gold platelet is Bunsen burnt (flame annealed) for 5 seconds and immersed in a piranha solution [$H_2SO_4$ (97% v/v) and $H_2O_2$(30% v/v) 3:1 v/v] for 20 min afterwards. The flame annealing can last for about 20 seconds, while the immersion in the piranha can last for 10-30 minutes.

then, the platelet is kept in boiling water for 10 minutes, then treated for 10 min in an ozone cleaner.

Alternatively, the gate electrode surface can be polished by a cyclic voltammetry based technique, commonly termed as 'electrochemical polishing'. Cyclic-voltammetry polishing can be carried out in three electrodes configuration using an electrochemical analyzer.

Ag/AgCl electrode in KCl solution is used as an electrochemical reference electrode, 0.5 M sulfuric acid ($H_2SO_4$ (97% v/v)) can be used as electrolyte in the electrochemical cell. The gate electrode 24 is placed as working electrode held in the solution using a standard electrode holder.

A platinum plate with an area approximately 1 to 100 times that of the gold working electrode 24 serves as counter-electrode. The potential is scanned between 0V to +1.5 V for at least 30 cycles. The scan rate is maintained at 0.1 V/s. Before every measurement, the electrolyte solution can be replaced with fresh solution and $N_2$ is bubbled through the electrolyte for at least 10 minutes to remove the dissolved oxygen contents.

After electrochemical polishing, the sensing gate electrode 24 is thoroughly rinsed with ultra-pure HPLC grade water and then with ethanol, and dried under a gaseous nitrogen ($N_2$) stream.

Alternatively, the sensing gate electrode 24 can be deposited or defined as a thin-film, by thermal evaporation or electron beam deposition of Ti (5 nm) and Au (50 nm) as well as by thermal evaporation through a shadow mask or by printing on a flexible substrate such as polyimide (Kapton®), mica, poly(ethylene 2,6-naphthalate) or polyethylene terephthalate, but also on rigid substrates such as Si/$SiO_2$ or glass or rigid plastic, or even the printed circuit board. This gate before the bio-functionalization is cleaned as follows: isopropyl alcohol (IPA) ultrasound bath for 10 min; UV/ozone surface cleaning for 10 min. The gold platelet was prior cleaned in a piranha solution ($H_2SO_4$/$H_2O_2$, 3:1 v/v) for 10 min and immersed in boiling HPLC water for 10 min, too. The described electrochemical polishing can be used also on the thin-film gate.

The chemical SAM (C_SAM) on the gold surface comprises a layer of mixed alkanethiols terminating with carboxylic functionalities. To this end, a 10 mM solution consisting of 10:1 molar ratio of 3-mercaptopropionic acid (3-MPA) to 11-mercaptoundecanoic acid (11-MUA) was prepared in ethanol. The cleaned gold surface was immersed in the 3-MPA and 11-MUA solution and kept in the dark under constant $N_2$ flux for 18 h at 22° C. The carboxylic groups are activated afterwards in a 200 mM 1-ethyl-3-(3-dimethylaminopropyl)-carbodiimide (EDC) and 50 mM N-hydroxysulfosuccinimide sodium salt (sulfo-NHS) aqueous solution for 2 h at 25° C.

The inventors have however observed that, in addition to the preferred parameters above, the same step can be practiced with a solution having a concentration in the range 10 mM to 100 mM, consisting of a 10:1 to 1:1 ratio of a 3-mercaptopropionic acid (3MPA) or mercaptans (thio-alcohols) to 11-mercaptoundecanoic acid (11 MUA) in ethanol grade, but also composed by the sole 3-mercaptopropionic acid or the sole 11-mercaptoundecanoic acid as well as by mercaptans (thio-alcohols) endowed of alcoxy chains of different lengths, and immersing the gate electrode 6 therein for a residence time comprised between 15 and 24 h and at a temperature of 15 to 28° C.

The strong gold-sulfur interaction results in the exposure of the carboxylic groups, activated subsequently by reacting the partially processed gate electrode as per the above in a 200 mM 1-Ethyl-3-(3-dimethylaminopropyl)carbodiimide (EDC) and 50 mM sulfo-N-Hydroxysuccinimide (sulfo-NHS) aqueous solution for two (2) hours at 25° C.

Again, the inventors have however observed that, in addition to the preferred parameters above, the same step can be practiced by reacting the gate electrode 6 in a 50 mM to 250 mM 1-Ethyl-3-(3-dimethylaminopropyl)carbodiimide (EDC) and 50 mM to 250 mM sulfo-N-Hydroxysuccinimide (sulfo-NHS) for a residence time comprised between 1 and 3 h and at a temperature of 22 to 28° C. An N-Hydroxysuccinimide (NHS) aqueous solution can be used instead of the sulfo-NHS one.

The human Immunoglobulin G (IgG) capturing B_SAM was generated, subsequently, through conjugation between the amine groups of the antibodies and the activated carboxylic groups on the gate surface, by immersing the gate in an anti-human Immunoglobulin (anti-IgG) phosphate buffer saline (PBS) solution for 2 h at 25° C. The solution was composed of 0.7 µM (0.1 mg/ml) of anti-IgG and 10 mM (KCl 2.7 mM and 137 mM NaCl) of PBS at a pH of 7.4 and an ionic-strength ($i_s$) of 162 mM. Afterwards, to saturate the unreacted sulpho-NHS groups, the anti-IgG SAM was further treated with ethanolamine 1 M in PBS 10 mM for 1 h at 25° C. This latter step is addressed as the surface "chemical-blocking" or just blocking stage. Finally, the bio-functionalized gate was immersed in a 1.5 µM (0.1 mg/ml) bovine-serum albumin (BSA) solution in PBS 10 mM for h at 25° C. This step of BSA physisorption is addressed as the "bio-blocking" of the gate surface. Both the conjugated anti-IgG and the adsorbed BSA form the herein addressed "B_SAM". The gate functionalized with both the C_SAM and the B_SAM is addressed in the text as the "SAM". For the control experiment the B_SAM is formed by conjugating BSA (instead of anti-IgG), followed by the surface bio-blocking with BSA.

The DNA capturing layer was deposited according to the following protocol. The gate surface with activated carboxylic groups was immersed in an Avidin (AV) phosphate buffer saline (PBS) solution for 2 h at 25° C. The solution was composed of 1.5 µM (0.1 mg/ml) of AV and 10 mM (KCl 2.7 mM and 137 mM NaCl) of PBS at pH 7.4 and $i_s$ 162 mM. Afterwards, to saturate the unreacted sulpho-NHS groups, the AV SAM was further treated with ethanolamine 1 M in PBS 10 mM for 1 h at 25° C. Finally, the gate was then immersed in a biotinylated single-strand DNA PBS solution 2 h at 25° C. The solution was composed of 0.5 µM of biotinylated single-strand DNA (sequence 5'-AGTGT-GAGTTCTACCATTGCCAAA) and 10 mM (KCl 2.7 mM and 137 mM NaCl) of PBS at pH 7.4 and $i_s$ 162 mM.

The described bio-functionalization procedure results in $10^{12}$ anti-IgGs or DNA capturing elements attached to the gate, so given that the gate area is about 0.6 cm², they are packed at the level of $10^4$ µm$^{-2}$, and more in general they are packed at a density comprised $0.1 \times 10^4$ µm$^{-2}$ and $10 \times 10^4$ µm$^{-2}$, preferably between $1 \times 10^4$ µm$^{-2}$ and $2 \times 10^4$ µm$^{-2}$.

The biosensor BS according to the invention is particularly suitable to be clustered into an array to provide an assay device. Such an array device enables multiplexing-type assays much like an Enzyme-Linked Immuno-Sorbent-Assay (ELISA) system.

The advantage of the array device according to the invention is that, differently from ELISA, the analysis is label-free and can be performed at the single-molecule detection level.

The array device structure is schematically depicted in FIGS. 4A and 4B, and the device overall is indicated by reference AD.

The assay device AD includes an array of biosensors BS, each being preferably independent from the other in the array. The assay device may be conceived as a simple ordinate array of single and separate biosensors BS, or—alternatively and more preferably—different degrees of integration may be envisaged for clustering the biosensors BS.

According to the embodiment of FIG. 4, the plurality of first wells 6 is provided by means of a plate 60, or lower plate, which is shaped as a pool and defines an interior volume configured to receive the first liquid 8, preferably HPLC-grade water or in any case an electrolyte with ionic strength lower than $10^{-2}$ mM. Laying on the bottom of the lower plate 60, and into the same, is as array (cluster) of resistor units RU. While here 24 (6×4) seats for the RU are shown, a preferred embodiment features 96 (12×8) spots to accommodate the RU (or the RUs) that will serve for given electronic-reference and sensing-gate stacked pairs. To perfectly match already existing machines that can handle in an automated fashion all the necessary functionalization, washing and sensing step in an ELISA assays, the array of FIG. 4A will be formed of 96 well 20 and the overall dimensions of the plate 60 and the matching lid 200 will be in the 8-15 cm×3-10 cm range, preferably 12.7 cm×8.5 cm.

The array of resistor units is preferably provided as a flexible but also a rigid substrate 12 (FIG. 4B) wherein resistor units are printed, i.e. wherein arrays (forming a matrix) of source and drain pads 2S, 2D, the source-drain channel 2, and respective semiconductor layer 4 are defined. The RU units are fabricated, preferably on substrate 12, by procedures such as inkjet, gravure, offset, flexo, (rotary) screen, microcontact, (Nano) imprinting; (Laser) transfer printing (of high performance circuits; dip-pen nanolithography; dry printing (Organic vapor deposition); hot embossing; laser processing (cutting sintering, patterning); stamping/die cutting; Slot-, dip-, spray-coating; R2R etching; lamination.

Each resistor unit RU may comprise one single resistor. Preferably, 1 to 10 separate (and separately electrically addressable) resistor units can be clustered together in an aggregate resistor unit RU associated to a single sensing-gate 24. To this end, the gate 24 preferably has a surface area ranging from 1 to 1,000 times the area of the interdigitated S and D pattern.

The resistor unit (RU) can be manufactured separately on a respective substrate 12, then the substrates may be attached to the bottom of the plate 60 by gluing, or else the cluster of resistor units may be printed directly on the bottom of the plate 60. Wherever manufactured the array of RUs the overall string of contact pad groups comes to define a connection interface to a socket or a connector (e.g. a terminal connector of a flat cable, for instance). The electrical connections (tracks) are all passivated afterwards with a solder resist to avoid their contact with either electrolyte 8 or 23.

Each of the resistor units RU is associated to a respective pair of source and drain pads 2S, 2D respectively. Preferably, as schematically shown in the figure, the pads may be provided group wise in ordinate and repeatable patterns that may serve as an interface to a flat cable or other type of terminal connector. The same pattern, as visible in FIG. 4B, is repeated here for all of the "columns" of resistor units RU.

An array of electronic-reference gates 14 is envisaged as a plate or sheet element GP in FIG. 4A as element 140. This element, better visible in FIG. 6B, provides once again a schematic plan view of an array 140 of electronic-reference-gate electrodes 14 connected by rigid wires. All the electronic-reference-gates are equipotential. The element GP may rest on a peripheral rim ($DS_1$) provided at the lower edge of the sidewall of the plate 60. The distance of the GP element from the RU unit array is given by the spacer frame $DS_1$=0.1-0.5 cm The electronic-reference-gates array can be made of bulk gold or once again provided as a rigid plastic or less noble core (Cu, stainless steel, titanium, aluminum, etc.) that is covered by a gold plating by means of the anodization processes detailed later on in the text. A contact pad 14P for the electronic-reference gate array (grid) 140 may be envisaged as depicted in FIG. 6. As the reference gates 14 are all preferably short circuited to each other, a single contact pad 14P may be enough. Additionally, just because the function of the gates 14 is that of an electronic reference, the array 140 may be even replaced by a single gate extending over the whole area covered by the single gates 14 (including interspaces there between).

An upper plate 200 in FIG. 4A, 4C provides, on its hand, a plurality of receptacles each embodying a respective second well so as to provide an array of second wells 20 for the underlying water-gated TFTs 16. In the embodiment of FIG. 4, the plate 200 is preferably an array plate featuring a matrix of wells—each well providing a single well 20—and wherein each well has its bottom replaced by a respective sensing gate electrode 24. In a preferred embodiment the upper plate (or lid) 200 includes an array of 96 (12×8) wells with an arrangement similar to a conventional "96-wells ELISA microplate".

Each well, either frustoconical or cylindrical in shape, has preferably the following dimensions: height 9-11 mm and diameter of 5-8 mm; preferably 10.3 mm and 6.9 mm. As anticipated the whole upper plate 200 may preferably exhibit overall dimensions of 12.7 cm×8.5 cm.

The upper plate or lid 200 sits on a second peripheral rim (spacer frame $DS_2$=0.2-1.0 cm, measured from the bottom of the well 6) provided by the side walls of the lower plate 60, so that the surfaces 26 of the sensing-gate electrodes 24 are exposed to the first liquid 8 in the plate providing the array of first wells. Moreover, the sensing-gates 24 should be aligned with the corresponding electronic-reference gates 14 and with the RU unit or cluster of RU.

Alternatively, stacking of the upper plate 200 onto the lower plate 60 may be provided via a pattern of pillars 18 formed on the bottom of the lower plate 60. A preferred option is that of providing four pillars surrounding each of the resistor units but clearly coarser or finer arrangements of pillars may be envisaged.

In embodiments wherein a pattern of pillars 18 is provided, such as in the lower plate of FIGS. 5 and 6, the cluster of resistor units is modified to adapt to the pillars. While of course no change is needed when the resistor units RU are printed directly on the bottom of the lower plate 60, whenever resort is made to a different substrate 12 for the cluster, a modification is required. FIG. 5A schematically shows a plan view of the lower plate 60 and the pattern of pillars 18. FIG. 5B shows a plan view of an array RP of resistor units provided as a rigid or flexible structure as described in the foregoing. The substrate of the cluster RP is provided with a pattern of holes 18H copying the pattern of pillars 18, as the same substrate is intended to fit onto the pillars for assembly of the array device AD.

FIG. 6A shows, accordingly, the assembly of the array of RP on the lower plate 60. FIG. 6B provides once again a schematic plan view of a first gate electrodes 14 array GP. The array GP 140 may comprise a plurality of holes matching the pattern of the pillars 18 to fit thereon, when provided. Alternatively, by making use of a spacer frame $DS_1$ arranged at the bottom of the lower plate 60 the pillars may be dispensed with and the array GP 140 may sit on the frame $DS_1$ which optionally could be even provided integrally with the side walls of the lower plate 60.

Note also that when the pillars 18 are provided, the first gate electrodes 14 may even be positioned independently on the respective resistor units, in a way similar to that shown in the foregoing FIGS. 1 to 3. The pattern of resistor units RU and superimposed gates 14 is shown in FIG. 6C.

Whatever the arrangement, the gate electrodes 14 of the array can be all connected together as the whole array GP 140 is made by a single piece of conducting material, optimally gold or, depending on the features of the driving circuit, be kept isolated from each other and addressed separately.

In the preferred embodiment, the electronic-reference-gate electrodes array 140 are all electrically connected to each other. In this case the GP element can be made of a bulk noble metal such as gold or it may comprise a rigid core made of plastic or a metal that is less noble than gold such as Cu, Ag, Ti, stainless-steel etc. which is fully plated or covered by a gold layer at least 0.05-2 µm thick, ideally 1 µm, by anodization procedures detailed later in the text.

In the case the reference gates are to be independent, any connection possibly existing there between (e.g. the substrate making up the cluster GP) is only structural, with no electrical connection features. This can be also realized on a circuit board with the relevant conductive tracks and pads as detailed for the array of the sensing-gates 24.

Figure 7:
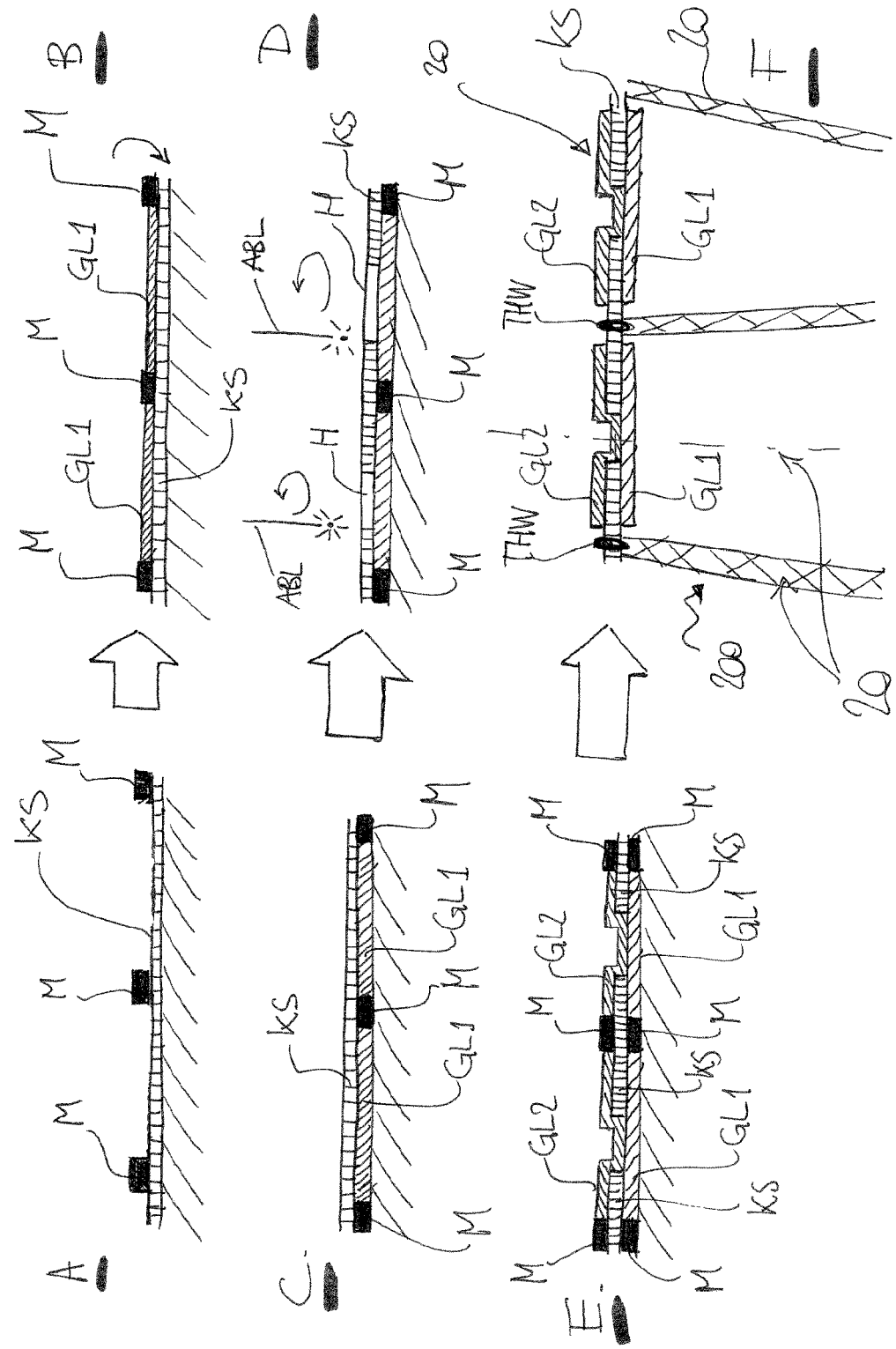
Figure 7H:
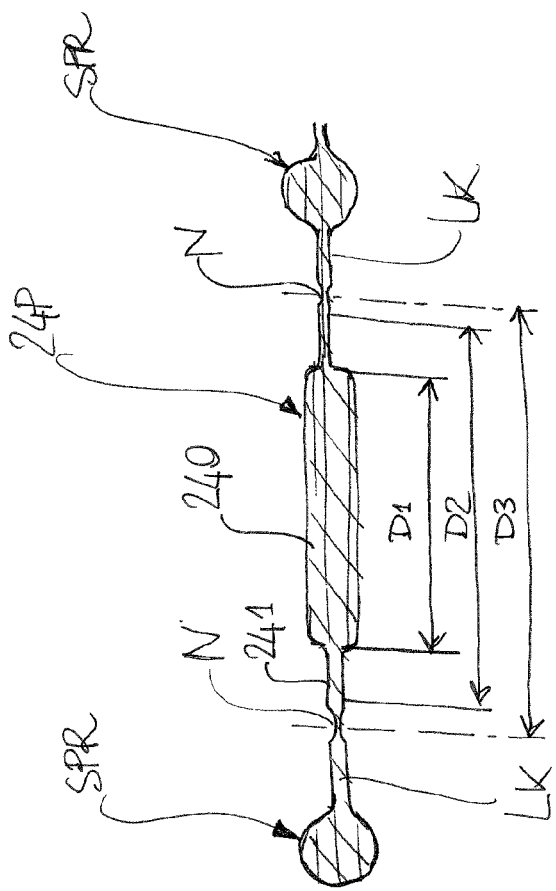

Turning now to the upper plate or lid 200, as anticipated in a preferred embodiment the same includes the plurality of wells shaped and arranged as the wells in conventional enzyme-linked immunosorbent assay (ELISA) microplates. Such an assay facility is well known in the art and will not be described in detail, but for reference a partial cross section of the receptacle walls is shown in FIGS. 7F, 7J and 7L.

This is a deliberate choice meant to resemble as much as possible an ELISA microplate, particularly but not restricted to, a 96-well one, not only in its appearance and its overall dimensions but most importantly in the way it is handled and operated. The aim is to provide clinicians with a tool that holds all the advantages of the electronic transduction of the e-SiMoA (single-molecule sensitivity, label-free fast detection etc.) but at the same time can be operated using the handling procedures, the exact same manual operations that are typically adopted to operate an ELISA assay.

What marks a difference between a conventional ELISA micro-plate and the upper plate or lid 200 is that the bottom wall of each of the wells is at least partially, preferably fully, provided by the gate electrodes 24, rather than the plastic plate itself.

In one embodiment, the upper plate 200 is provided with a pattern of through wells 20 featuring bulk gold gate electrodes 24 individually applied to each of the bottom sections of the well. Each sensing-gates 24 will be addressable by means of connections. The connection between the gate electrode 24 and the well walls may be provided by means of liquid tight glue and/or sealant to ensure liquid tightness of the second wells.

In the array configurations AD these connections are routed on a board connected to the array driving circuit. This will also be the case for each of the S & D electrodes of each of the RU.

The above embodiment is however susceptible of requiring highly qualified labour to be assembled, and is therefore mainly envisaged for tailor made array devices manufactured in small production lots.

In another embodiment, which is the subject of the sequence of steps illustrated in FIGS. 7A to 7F, the application of the gate electrodes 24 as the bottoms of the receptacles of the upper plate 200 is performed differently. Note also that either technique shown in FIGS. 7A to 7F, and 7G to 7J may be used whenever—in a single biosensor BS—the gate electrode 24 is not made from a solid piece of gold, but rather features a core substrate and first and second layers of electrically conductive material, preferably gold or other noble metals, fully covering all the surfaces of the core substrate and in contact to each other so as the surfaces 28 and 26 of the gate 24 are equipotential.

With reference to FIG. 7A, a core substrate KS made—as an example—of polyimide (Kapton®), is laid on a working surface. The side of the substrate KS opposite to the working surface is treated with a mask M. Despite visible in cross section only in the figures, the mask M has a circular mesh pattern, meaning by this that the layer making up the mask M is interrupted by voids having the size and shape of the inner diameter of the bottom end of the receptacles 20 of the upper lid 200, hence circular voids.

With reference to FIG. 7B, once the mask M is set, a first gold layer GL1 (this applies identically whatever the electrically conductive material chosen) is deposited over the substrate KS, thus filling the voids in the mesh of the mask M and generating a pattern of circular gold patches over a first side of the substrate KS.

The partially coated substrate KS is then flipped (FIG. 7C), preferably leaving the mask M on, thereby exposing the pristine polyimide or Kapton® surface on the formerly hidden side of the substrate KS.

By making use of ablation means ABL (FIG. 7D), such as laser beams or selective chemical etching, through holes H are opened in the substrate KS. Laser ablation of polyimide or Kapton® thin films can be easily achieved using a variety of lasers, e.g., ultraviolet pulses of 248 nm or 308 nm radiation (~20 ns long) produced by excimer lasers, or microsecond long pulses obtained by chopping with an optical chopper the emission of ultraviolet or visible lines of continuous wave Argon ion lasers, or else using infrared 9.17 µm laser radiation (~170 ns long) of carbon dioxide lasers. Power and/or focus of the laser ablation beam shall be adjusted so as not to damage the underlying gold layer GL1. Selective chemical etching of polyimide or Kapton® layers can be easily carried out using contact photolithography and standard chemicals, such as a solution of 6% potassium hydroxide (KOH) in a solvent mixture of 80% ethanol and 20% water.

Then, FIG. 7E, another identical mask M is applied on the top, uncoated, surface of the substrate KS and a second layer of electrically conductive material, once again preferably gold or other noble metals, is deposited on the exposed surfaces. Note that since deposition leaves a uniform thickness of coating material, the layer GL2 will exhibit embossments at the holes H.

The substrate KS is now in core position between the layers GL1 and GL2, and the masks M are then removed.

Next, FIG. 7F, following removal of the masks M the uncoated areas of the substrate KS define a pattern overlapping with the bottom end rims of the receptacles/pools 20. Thermal welding THW is then applied at the uncoated areas and with a circular pattern matching those of the rims, thereby permanently (an in a liquid tight fashion) joining the substrate KS with coating layers GL1 and GL2 to the receptacles 20.

The coatings GL1 and GL2 are hence made equipotential owing to the conductive bridge extending through the core substrate KS at the holes H.

With reference to FIGS. 7G to 7J, another preferred technique for manufacturing the sensing gate electrodes 24 is shown in therein.

Figure 7G:
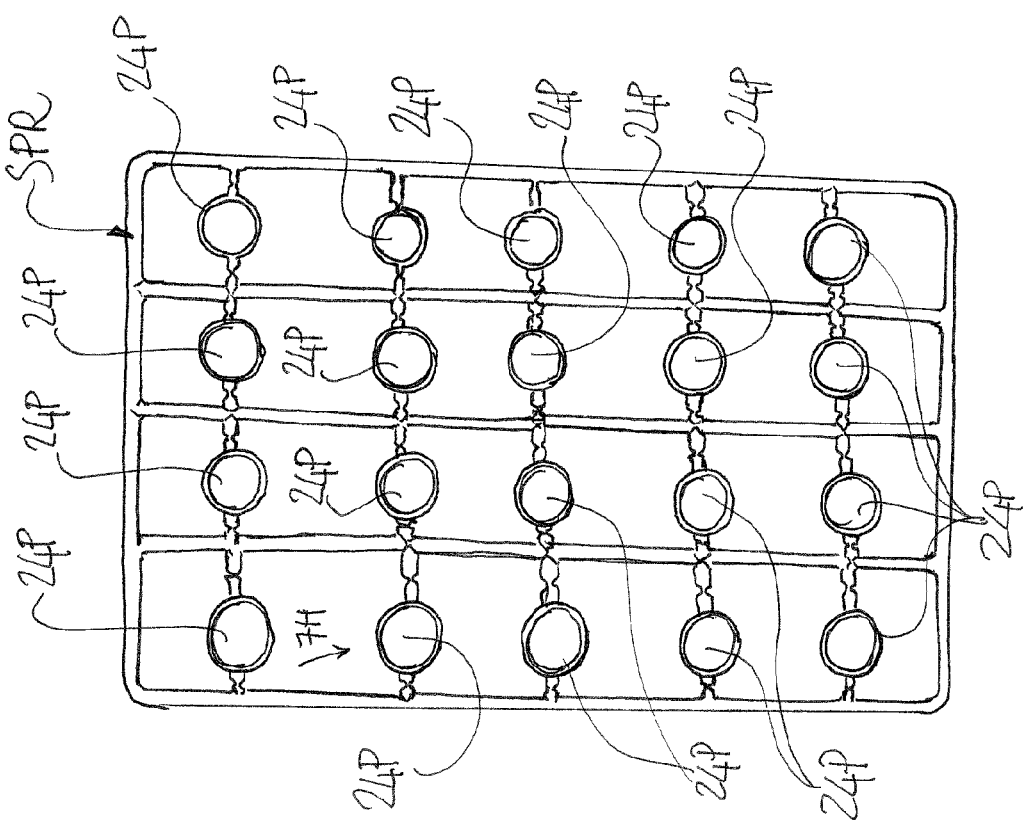
Figure 7J:
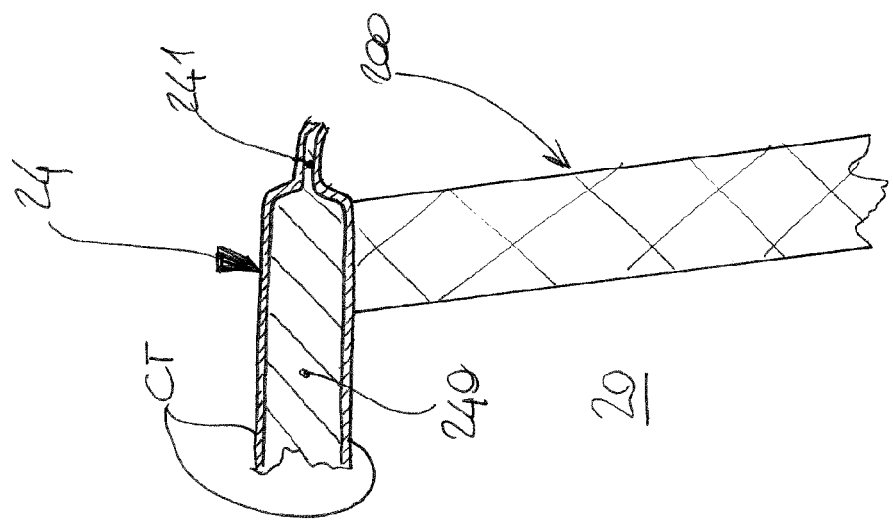

Instead of starting from a core substrate as per the technique shown in FIGS. 7A to 7F, the starting condition is that of a cluster of second gate precursors 24P formed e.g. by injection molding (in case of plastic materials) or casting (in case of metal materials), and held together by a sprue SPR (FIG. 7G).

The plastic materials can be rigid or flexible such as for instance polyimide or Kapton® (which is a poly (4,4'-oxydiphenylene-pyromellitimide). The Kapton® precursor is a "poly(amic acid)" which is soluble and can be injected into the mold. The final step is a treatment at 200-300° C.). The resulting standard flexible film is generally between 25 µm and 100 µm. The metal material can be a flexible aluminum foil that is shaped in its liquid state by molding as well.

Alternatively, the shaping of the polyimide or Kapton® as well as the aluminum foil (25-100 µm thick, preferably 50 µm thick) into the shape shown in FIGS. 7G and 7H can be done by cutting the foil by means of laser cutting procedures.

A further alternative can be to make holes (by laser ablation of selective chemical etching) as described earlier in the text) into the polyimide or Kapton® circular elements of the precursor 24P before the gold coating ids performed. The pattern of the precursors 24P coincides with the arrangements of the bottoms of the wells 20 on the plate 200.

FIG. 7H shows a cross section of one of the precursors 24P prior to further processing steps, to better understand certain features thereof. Each of the precursors 24P is a circular elements linked to the sprue SPR preferably by a pair of links LK. The precursor 24P per se comprises a central disc-shaped portion 240 having a first thickness and bordered by a peripheral flange 241 having a second thickness, lower than the first thickness. The peripheral flange 241 is the portion of the precursor 24P that is actually connected to the sprue SPR. Connection occurs with the interposition of a notch N, which provides a weak point for encouraging separation from the sprue SPR when needed.

Three reference diameters may be named on the precursor 24P, namely:
- an inner diameter D1, which is the diameter of the disc-shaped portion 240,
- an outer diameter D2, which is the (outside) diameter of the peripheral flange 241, and
- a separation diameter D3, which is the diameter of a reference circle whereat the notches T are positioned. Note that in case of an irregular sprue, the diameter D3 may actually not apply.

In a first processing step, the entire surface of the sprue SPR and the precursors 24P is coated with a gold layer (or other precious metal layer) CT. Coating may even occur by plating in case the sprue SPR and the precursors are made of metal material.

The coating of the aluminum precursor 24P will be carried out similarly to what reported in the book "Trattato di Galvanotecnica I", E. Bertorelle, Hoepli; 4th edition (10 Jun. 2016), ISBN-13: 978-8820374983. In particular, the metallization typically consists of the following steps:
1) electrode sonication in detergent solution (5% in water at 70° C.) for 3 minutes;
2) electrode sonication in detergent solution (2% in water at 60° C.) for 3 minutes;
3) washing with pure water:
4) pickling in acidic solution (nitric acid 60%+fluoridric acid 7%) for 30 seconds;
5) washing with pure water;
6) case hardening with zinc;
7) washing with pure water;
8) galvanic deposition of copper under alkaline conditions (electrolyte typically composed of copper cyanide+ potassium cyanide, t=40-50° C., current density=1A/dm$^2$ pH=10.5-11, film thickness in the few micron range);
9) washing with pure water;
10) galvanic deposition of copper under acidic conditions (electrolyte typically composed of copper sulphate+ sulphuric acid+sodium chloride, room temperature, current density=3-4 A/dm$^2$ pH=1, film thickness in the few micron range);
11) washing with pure water;
12) galvanic deposition of gold (electrolyte typically composed of KAu(CN)$_2$ phosphate buffer solution, pH=5-6, t=60-70° C., current density=1-2 A/dm$^2$ film thickness in the range comprised between few tents nm to 2 micron)

These steps are slightly adjusted as a function of the composition of the starting Al substrate (concentration of impurities/minor elements, etc).

For coating the Kapton® substrate foreseen for the 24 P, conditions follow what reported in the chapter "Polyimide film metallization", Metallized Plastics 2: Fundamental and Applied Aspects, Volume 2, K. L. Mittal Ed, Springer Science & Business Media, 11 Nov. 2013—477, •ISBN 978-1-4899-0737-0 and particularly consist of the following steps:
1) polymer film cleaning by washing with aqueous alkaline solution;
2) electrochemical charge injection into the film by means of potassium or tetramethylammonium salts of V(II) EDTA-2 species;
3) oxidation of the film in a copper oxalate solution
4) thick copper film formation by immersion in electroless copper solution (typically up to few hundred nm);
5) galvanic deposition of gold (same as step 12 of the previous procedure for Al film coating).

These steps are slightly adjusted as a function of the composition of the starting plastic substrate; in particular, a chemical etching might be introduced after step 1 to improve substrate initial roughness and the consequent adhesion of the metallic coating.

Figure 7I:
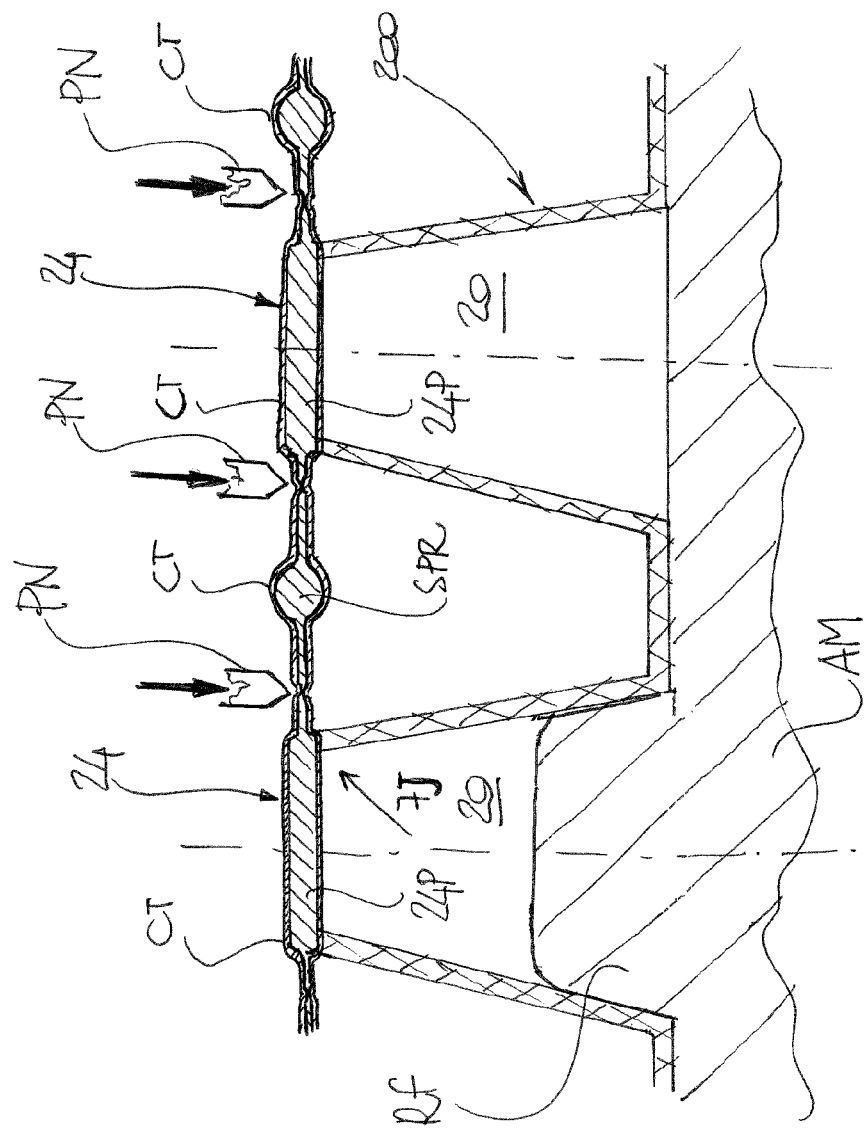
Figure 7L:
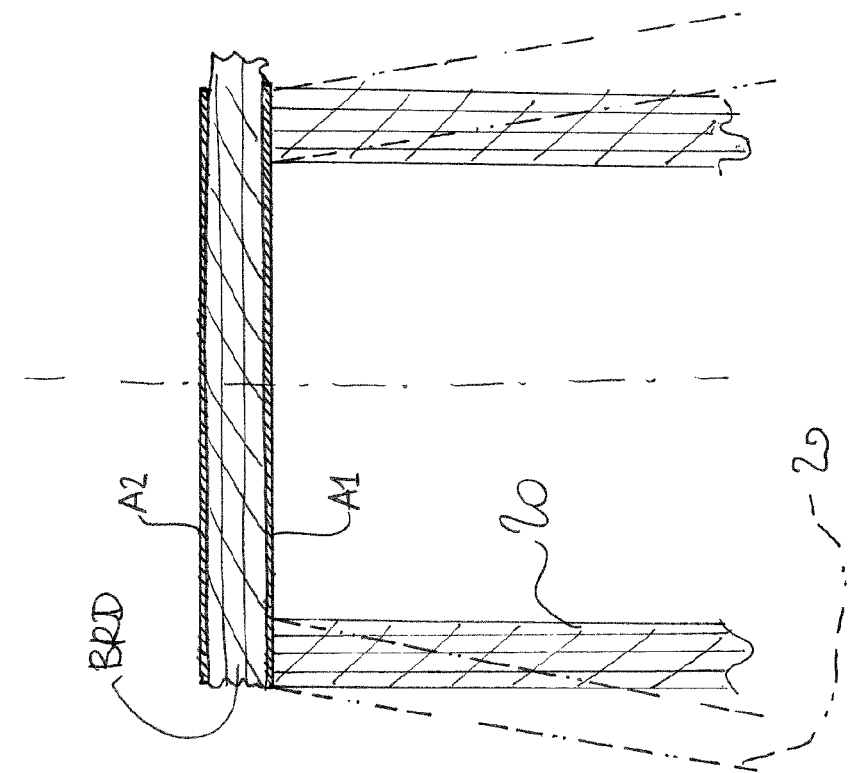

The coated sprue and precursors 24P are shown in FIG. 7I, which also illustrates the next processing step. Once coated, the sprue SPR is transferred to the plate 200, which similarly to that shown in FIGS. 7A to 7F is provided with through wells 20 (i.e. bottoms commonly provided in a standard ELISA plate are dispensed with already at the molding stage of the plate 200).

The plate 200 is set upside down (i.e. with bottom portions up) on an auxiliary mold provided with a plurality of reliefs RF configured to penetrate at least partly into selected wells 20, to keep the plate 200 in position. Note that it is not necessary for the reliefs RF to go all the way through the wells, nor it is necessary to have an equal number of reliefs RF and wells 20.

As visible in FIG. 7I, the diameter D1 shall be chosen so as to be at least equal to the outer diameter of the bottom portion of the well 20, in order to ensure an optimal sealing once the freshly-formed electrodes 24 (coated precursors 24P) are set onto the well bottoms. The sprue is in fact superimposed to the pattern of wells 20 by making sure that the axis of the portions 24 lines up with the longitudinal axis of a respective well. If the diameter D1 is chosen according to the above, the contact between the gate electrode 24 and the corresponding end (bottom) portion of the well 20 will occur all at the disc-shaped portion 240. The contact interface is thus more uniform, and allows for a stronger bond between the electrode 24 and the well 20.

Next, an array of cutting tools are positioned at corresponding notches N and lowered in order for the links LK to be cut and the electrodes 24 severed from the sprue SPR. Note that by providing the peripheral rim 241, the cutting and severing action invariably takes place at a distance from the connection interface between the electrode 24 and the bottom end of the well 20, thereby also discouraging any geometric distortion (with subsequent weakening of sealing action) due to cutting. The resulting coupled, cut and severed electrode gate 24 is shown in partial cross section in FIG. 7J. Both opposite sides of the so-formed electrode 24 are equipotential due to continuity of the layer CT across the surface of the electrode. When the gates 24 are severed from the sprue SP, the severing points on the broken connection links may be used as a starting point for routing electrical connections to the gates 24.

Note also that even the gates 14 may be provided in a way similar as that described herein for the gates 24, i.e starting from precursor gates on a sprue, which are then coated in precious metal(s). Note also that, on account of the reference gates allowing for a short circuit connection to each other, there is also no need to sever the coated precursors (i.e. the finished gates 14) from the sprue.

Figure 7K:
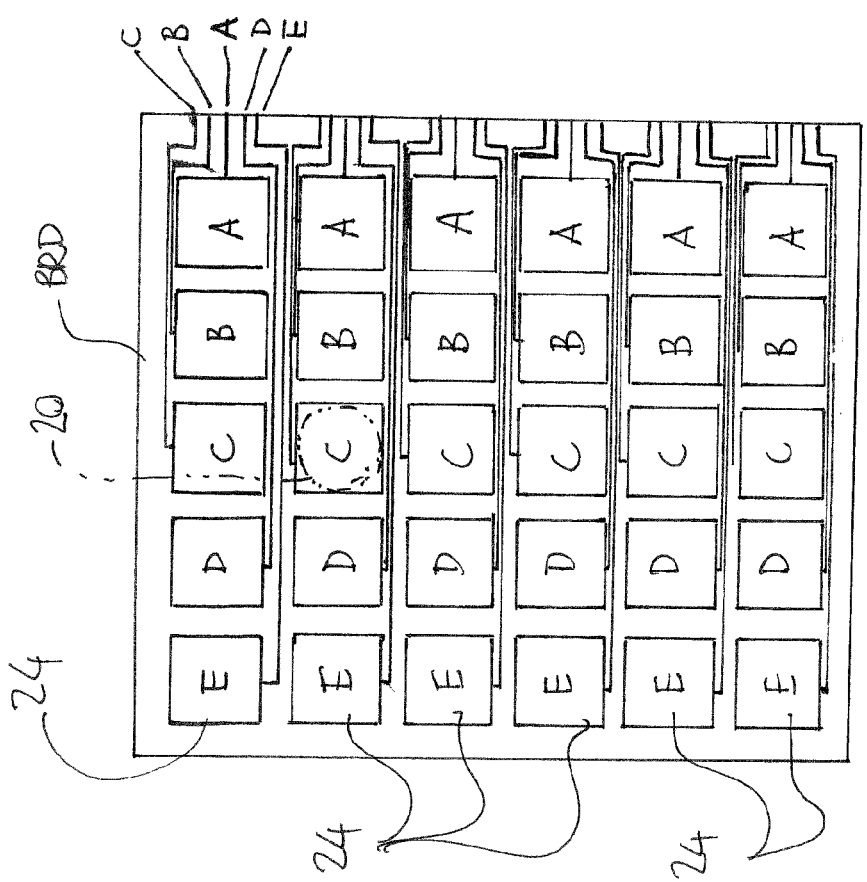

Yet another preferred technique for manufacturing the sensing gate electrodes 24 is illustrated in FIGS. 7K-7L.

A circuit board BRD is provided extending over the entire area of the upper plate 200. The board substrate can be made of flexible or rigid substrate such as Kapton® or of the typical FR 4 or brebeg. A twin array of gold (or other noble metal) gate electrodes 24 (or gate 14) is printed or otherwise deposited on both sides of the board BRD, wherein the twin arrays are overlapping in the plan view so as to provide the same pattern on both sides. For better references, the array is partitioned in rows, each featuring five sensing-gate gate electrodes 24 (or alternatively electronic-reference gates 14) indicated by auxiliary numbers A, B, C, D, E. Electrical connections are likewise printed or otherwise deposited on the board, and are grouped in correspondence of a side of the board BRD, wherein grouping occurs on a row-by-row basis. The electrical connections are all passivated afterwards with a solder resist to avoid their contact with either electrolyte 8 or 23. This means, with reference to FIG. 7K, that in the purely illustrative example considered, six groups of five contact pads are printed on both sides of the board BRD and at the same locations. Clearly for the 96-well configuration 96 couple of sensing-gates 24 will be deposited. In the sensing gates 24 each contact is associated to one (and one only) gate—correspondence being established by identical letters—and the overall string of contact pad groups comes to define a connection interface to a socket or a connector (e.g. a terminal connector of a flat cable, for instance).

The board BRD of the gates 24 is then attached to the upper plate 200 by making sure that each well 20 is contained (inscribed) within a quadrangular (or else circular, in certain alternative embodiments) gate electrode 24 for subsequent connection to the walls—which may be cylindrical or conical—of the wells 20 as shown in FIG. 7L. The attachment of the board BRD of the gates 24 is also to be water tight so as wells 20 are sealed in the bottom and can hold the water poured into them.

This also implies that, being the same pattern of gate electrodes 24 (A-E) and contact pads A-E printed or otherwise deposited on both sides, when the board BRD is plugged to a socket or to a connector, the conductive terminal ends provided therein will operate as a clamp bridging both sides of the board BRD. That is because each second sensing-gate electrode 24 (this applies likewise when a single gate system like the biosensor BS is considered instead of an array device) includes first and second faces A, B, C, D, E on opposite sides of the circuit board BRD with electrical connections departing from each face and ending at corresponding locations on the opposite sides of the circuit board BRD. Each of the printed electrode gates 24 of each pair lying on opposite sides of the board BRD will therefore operate as a single gate electrode 24 with equipotential sides, just as described above. The connections to each sensing-gate 24 will indeed be used to bias the same by applying the selected $V_G$ (gate voltage) biases.

As a general design guideline, whatever the technique used to provide the array of gate electrodes 24, the gates in the array 24 are fully independent from each other, the same applying to the resistor units RU (or clusters of resistor units) associated to the respective gate electrodes 24 (one-to-one association, be it on a resistor unit basis or on a cluster basis).

The reference gates 14, on the contrary, may be all short circuited as already anticipated. Nevertheless, they can be wired independently of each other in certain embodiments.

Similarly, to what described for the single biosensor BS, the wells 20 are used at first to pour those of the solutions 23 needed to bio-functionalize the already gold-plated and cleaned gate 24 to generate the layer of bio-recognition elements 30 composed of the C_SAM and of the B_SAM. In general, the C_SAM layer will be the same for all the sensing-gates. The chemical bio-functionalization process can be carried out on the gate surface 28, before metallizing the surface 26 and before placing the gates on the bottom of each well by the procedures reported earlier on in the text. The activation of the C_SAM, the conjugation of the B_SAM layer along with the chemical and biological blocking of the surface is carried out after the gates are placed at the bottom of the well by dispensing in the wells all the needed solutions 23 and by washing between each step.

The B_SAM can be different for each of the wells 20 composing the array to endow the system of multiplexing properties namely to sense and quantify different biomarkers. This multiplexing feature will be implemented in the same way as for a standard label-needing ELISA assay. After the layer 30 is deposited, the wells 20 are filled with the standard solutions or with the bio-fluids to be analyzed. Each B_SAM is incubated for a time ranging from 1 to 30 minutes, preferably 10 minutes, with the solution to be analyzed or with the standard solutions. The standard solutions are used for calibration and biomarkers quantification purposes. Then the elicited solutions are removed and the well is washed thoroughly first with the PBS and with HPLC water afterwards. At the end when the water-gated TFT 32 is operated, the wells 20 are filled up with pure HPLC-water.

So the array system here proposed can be operated very much like an ELISA microplate with the same multiplexing functions but it has the following major advantages:
- it is much more sensitive as it reaches single-molecule detection level;
- it is much faster as it is label-free;
- it is equally selective as biological recognition elements are integrated into the device with procedures similar to those used in the ELISA assay;
- it functions equally well with proteins, peptides and DNA strands.

Figure 8:
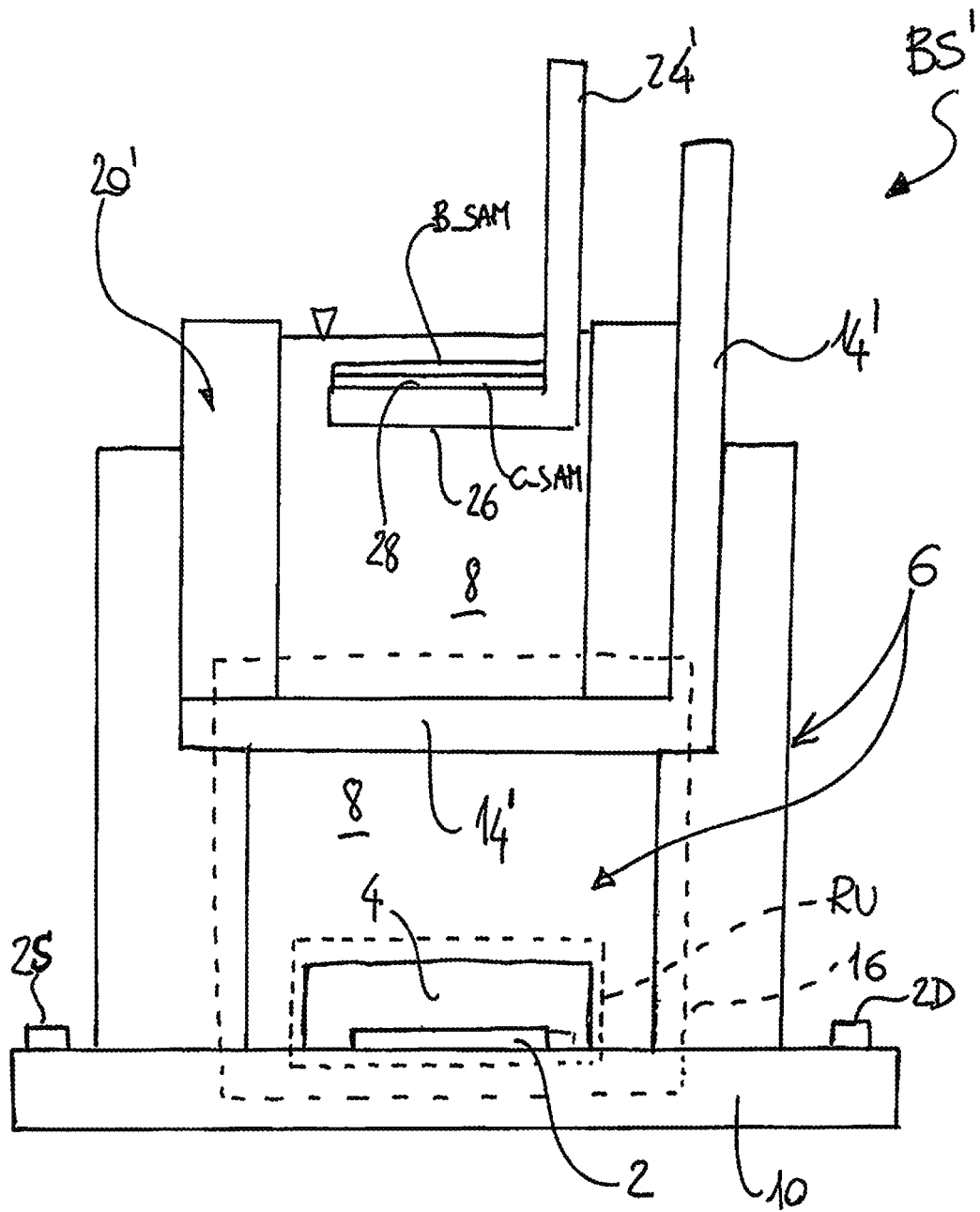

The important improvements, in terms of sensitivity and assay time, compared to the state-of-the-art label-needing techniques that we gained with such an electronic single-molecule assay (e-SiMoA) array system here proposed have been demonstrated using a test device BS' schematically shown in FIG. 8. The references identical to those already used herein designate the same components already described.

The main differences between the test biosensor BS' and the embodiments of the biosensor BS disclosed essentially apply to the gate electrodes 14 and 24, and—mainly—to the second pool area.

The interdigitated electrodes 2 are connected to larger pads 2S, 2D by means of long arms, so that the S and D contacts can be taken by means of probes. Preferably the test biosensor BS' comprises six source and drain interdigitated patterns realized by means of photolithography on a Si/SiO$_2$ pieces of wafer glued on a glass substrate. The details of the S&D structure are the following. A prior deposited layer of titanium (5 nm) served as adhesion layer. Afterwards a gold deposit of 50 nm is carried out. The distance between two differently biased fingers defines the channel length (L=5 μm), while the perimeter of all the equipotential fingers is the channel width (W=1280 μm).

The geometrical features implemented envisage gates 14' that are much larger than each S&D pattern areas (approximately 100:1), thus enabling each of the resistors units RU to be gated through the same electronic-reference gate 14' and the sensing gate 24'.

Such a design enables the switching form one resistor unit RU to another (under the same gate) in case a resistor fails. The gates 14' and 24' are rectangular rigid gold laminas and are L-shaped so as the squared horizontal 'feet' of the "L" (0.8×0.5 cm$^2$ wide 0.3 mm thick) is the actual gate area, while the vertical "leg" of the "L" enables the contact to be taken directly by a probe. In the array configurations AD these connections are routed on a board connected to the array driving circuit. The first electronic-reference gate electrode 14' is once again set at a distance above the resistor unit RU A P3HT-ZnO nanocomposite produced as reported in the previous text, is spin-coated on the interdigitated electrodes area and a polydimethylsiloxane (PDMS) circular wall providing the sidewall of the well 6 is glued on the Si/SiO$_2$ substrate around all six the source and drain interdigitated contacts. The thickness of the wall is ca. 4 mm while the maximum internal diameter of the wall is 12 mm. Alternatively a bare P3HT layer can be used as well. In this case a P3HT solution (2.6 mg ml$^{-1}$ in 1,2-dichlorobenzene) filtered with 0.2 μm filter was spin-coated at 2×10$^3$ r.p.m. for 20 s and annealed at 80° C. for 1 hour.

This results into a sealed first well 6 approximately 7 mm high, with the resistor units RU sitting on the bottom thereof, that contains the gating electrolyte 8, namely the HPLC-grade water. After the gluing of the PDMS circular wall, the well is filled with water at a height of approximately 0.7 cm from the bottom. At this level, the thicknesses of the PDMS internal perimeter wall is reduced to 8 mm to provide a circular, peripheral, rim inside the well onto which the squared foot of the L-shaped reference gate 14' can sit. A second well (communicating with the first one) is generated whose height is 7 mm.

The electronic-reference gate 14' is then secured in its position by inserting a rigid hollow plastic tube 20', which sits on the reference gate 14' "feet" at a position corresponding to that of the second well 20 of the biosensor BS. In the case of BS', however, there is no proper second well as the reference gate 14' does not seal the bottom of the tube 20'. Nevertheless, the biosensor BS' of FIG. 8 retains another feature common to the biosensor BS and providing the technical effect sought after by the invention: a stacked arrangement of the sensing gate 24' and the reference gate 14'.

The second well, that will contain all the solution 23 (for the C_SAM and B_SAM deposition as well as the analyte (biomarker) standard solutions or the real bio-fluid to be analyzed) may be arranged as a separate pot in which the gate 24' can be exposed to the solution needed for its bio-functionalization as well as to be exposed to the solutions to be analyzed. Thus in the biosensor BS' the second well only comes into play at for functionalization of the gate 24' as well as to its exposure (in fact incubation) to the analyte (bio-marker) solution to be analyzed or to the standard solutions of the same bio-marker.

The well 6 is then completely filled up with solution 8 that is only HPLC water and the already bio-functionalized gate 24', before and after incubation, is immersed into the water.

Such a device structure works on the same principle as those disclosed in the foregoing, the main difference being that there is no second well and the already bio-functionalized gate 24' is removed at each incubation step, washed and positioned back for the measurement.

Figure 8A:
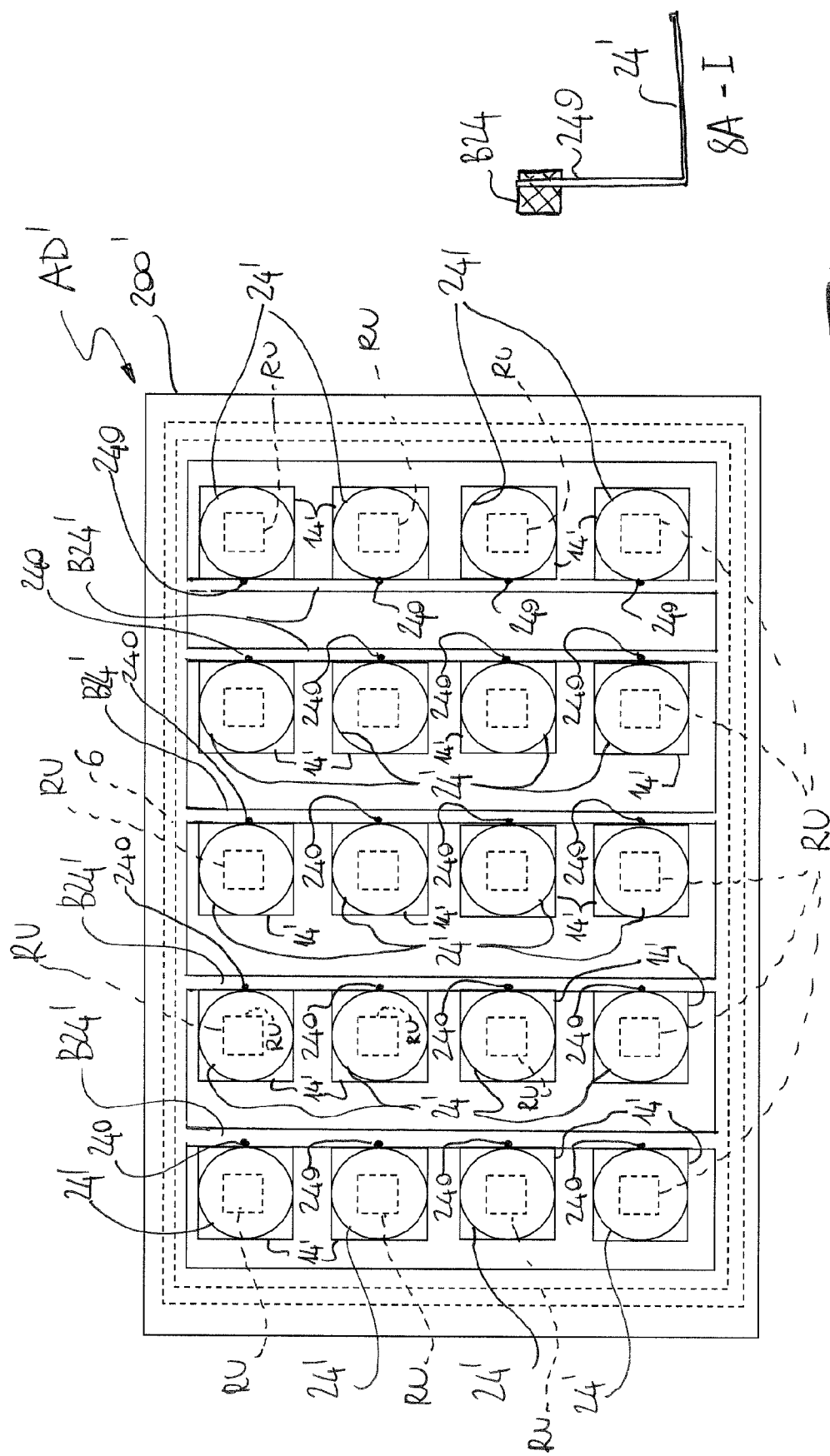
FIG. 8A shows an array device based on the biosensor of FIG. 8

Additionally, the biosensor BS' can be a modular unit for an array device AD' which is shown in FIG. 8A. The array device AD' retains all of the components, material and arrangements visible through FIGS. 4, 5, 6 as far as the lower plate 60, the resistor units RU and the reference gates 14' are concerned (note that in this case it is more convenient to have the reference gates 14' on a film/plate 140 rather than shaping the same into a "L"), but clearly it gets different above the reference gates 14'. The upper plate or lid 200 visible in FIGS. 4A and 4C is replaced by an upper plate 200' which is essentially configured as a quadrangular (preferably rectangular) framework stacked on top of the lower plate 60 wherein the longest opposite sides are bridged by bridging members B24 (the overall appearance is that of a grid with rectangular slots). The bridging members B24 serve as supporting beams for sensing gate electrodes 24', which are each provided with a connection post 240 (orthogonal to the gate surface) fixed to the bridging members B24. One preferred technique may include co-moulding of the post 240 into the material of the bridging members B24. An exemplary arrangement of the gates 24' on bridging members B24 is shown in FIG. 8A-I, wherein the generally "L" shape (at least in side view) of the gate 24' is also shown. Not only this, the bridging member B24 may also serve as routing facility for electrical connection to the gates 24'.

As visible form FIG. 8A, the gate electrodes 24' are essentially hanging from the plate 200' above the respective reference gates 14' (which may even be replaced, as described, by a single reference gate 14' extending over the entire area of the gates 24 in the array device AD'), and are as such exposed to the interior of the well 6 and—in use—to the gating electrolyte 8. The surface of the gates 24' visible in FIG. 8A is—clearly—that hosting the layer of biological recognition elements. The whole system of gates 24' is brought, maybe by a mechatronic arm in an automated fashion, into an array of "side" well 20 to be bio-functionalized. Both or either one of surfaces 26 or 28 can be covered by layer 30. The gates 24' are exposed afterwards to the standard solutions or to the real bio-fluids to be analyzed that can be different for each gate. The sensing-gates 24' can be made out of "bulk" gold or of a less noble metal electroplated with gold and can be reused as the layer 30 can be totally removed after the already described cleaning procedures.

More in general the in the array device AD' the upper plate (200') may be provided as a framework-like structure with bridging members B24 extending across the same (not necessarily across opposite long sides). The bridging members B24 support a pattern of second gate electrodes 24' above one or more corresponding first gate electrodes 14' housed in the lower plate 60, with the upper plate 200 stacked onto the lower plate 60.

Operation of each sub-unit of the array device AD' is identical to what already described in respect of the biosensor BS'.

Whatever the embodiment, and also independently of whether executed on a single biosensor or with the array device AD, AD' the sensing measurements are carried out as reported in the following.

The water-gated TFT 16 current-voltage curves are measured with a semiconductor parameter analyser equipped with a probe station, in air and at RT (20-22° C.). The TFTs were tested in the common-source configuration. For the transfer characteristics the source-drain current, $I_D$, is measured as a function of the gate-bias, $V_G$ (ranging from +0.1 to −0.5 V) at a constant drain voltage of −0.4 V. The upper and lower limit of the cycling procedure will depend on the potential window of electrochemical inertness of the material choses as semiconductor channel material 4. The voltage ranges were tuned to minimize the gate leakage current ($I_G$) associated with electrochemical processes that could produce oxidative degradation of the SAM layer and of the P3HT+ZnO-NPs semiconducting nanocomposite. To control and minimize such processes $I_G$ was always acquired along with $I_D$ and all the curves were measured in the forward and reverse mode to evidence the occurrence of hysteresis. When and hysteresis was persistently observed, the potential gating voltage window was reduced until any spurious effect and the anomalous hysteresis disappeared.

Figure 9:
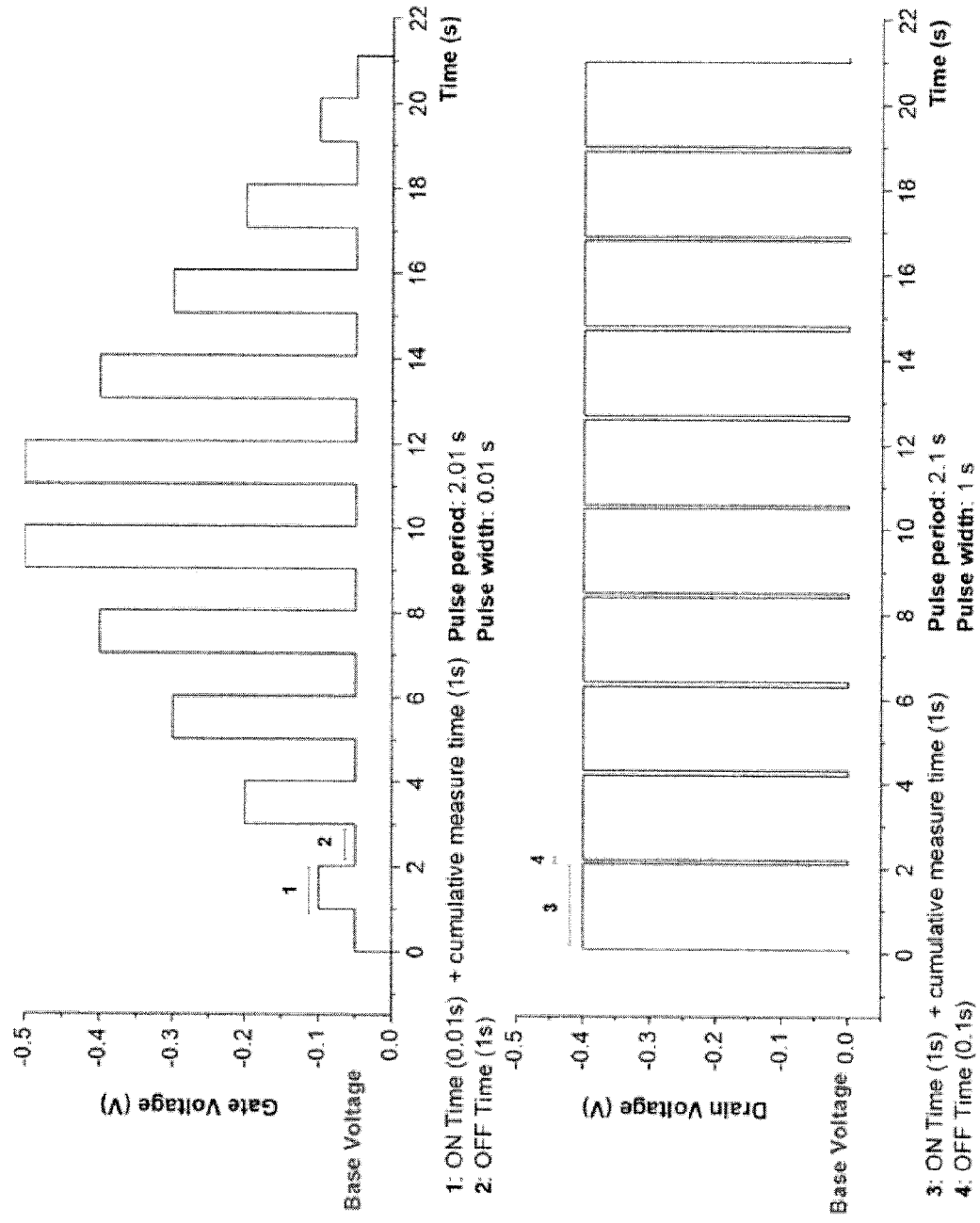
FIGS. 9 to 14 show experimental results based on measurements executed with the biosensor according to the invention.

At first the water-gated TFT 16 needs to be stabilized; namely, the $I_D$ current flowing in the semiconductor 4 TFT channel needs to be constant for a sufficiently long time. The stabilization procedure can involve the pulsed biasing of the reference gate 14 and of the drain electrode with the duty-cycle shown in FIG. 9. In the upper panel the pulsed duty-cycle of the gate-bias, $V_G$, while in the lower panel the corresponding pulsed duty-cycle applied to the drain electrode, $V_D$, are shown. The gate-bias pulse output reaches to the imposed level during the pulse on-time (1 in FIG. 9). The current is measured when the on time expires and before the transition to the off-time level is accomplished (2 in FIG. 9). This effectively increases the on-time by the amount of time required to make the measurement (cumulative time), which is 1 s. During the off-time, the pulse output returns to the specified base voltage level, namely to 0 V. When a sweep forcing function is used, the pulse output steps to the sweep step levels during the pulse on-times. During the off-times the pulse output returns to 0 V. The $I_D$ current is measurement after each on-time period expires and before the pulse transitions to the off-time level.

In the present case the duty-cycle is set in the dual sweep mode. Namely, the cycle continues by going back to the upper voltage level and then step down to the start voltage level. In this case, the pulse on- and off-times determine the pulse period and the pulse width as follows: −pulse period: on-time+off-time+cumulative time; −Pulse width: on-time. As already addressed the gate voltage is swept from +0.1 to −0.5 V with a step of −0.01 V.

The ideal features of the duty cycle are: $V_G$ ranging between +0.1 V and −0.5 V; − pulse period: on-time+off-time+cumulative time=2.01 s; −Pulse width: on-time=0.01 s. However, the following also holds: $V_G$ ranging between whatever interval included in: +1.5 V and 1.5 V; −pulse period falling in the interval 0.01 s to 10 s; Pulse width falling in the interval 0.001 s to 1 s.

$I_D$ was stabilized by cycling the measurement of the transfer curve of the P3HT+ZnO-NPs nanostructured channel materials carried out with the reference-gate 14', until a stable $I_D$ level is reached. During this process, the low-mobility trap states of the channel materials are filled, eventually leading to a stable $I_D$ value. The stabilization of the current is carried out by measuring the transfer curve with the already described pulsed-duty cycle, in the forward and reverse run, until a few stable traces were seen. To monitor the stabilization of the current, the maximum value of $I_D$ at $V_G$=−0.5 V is plotted versus time.

Figure 10:
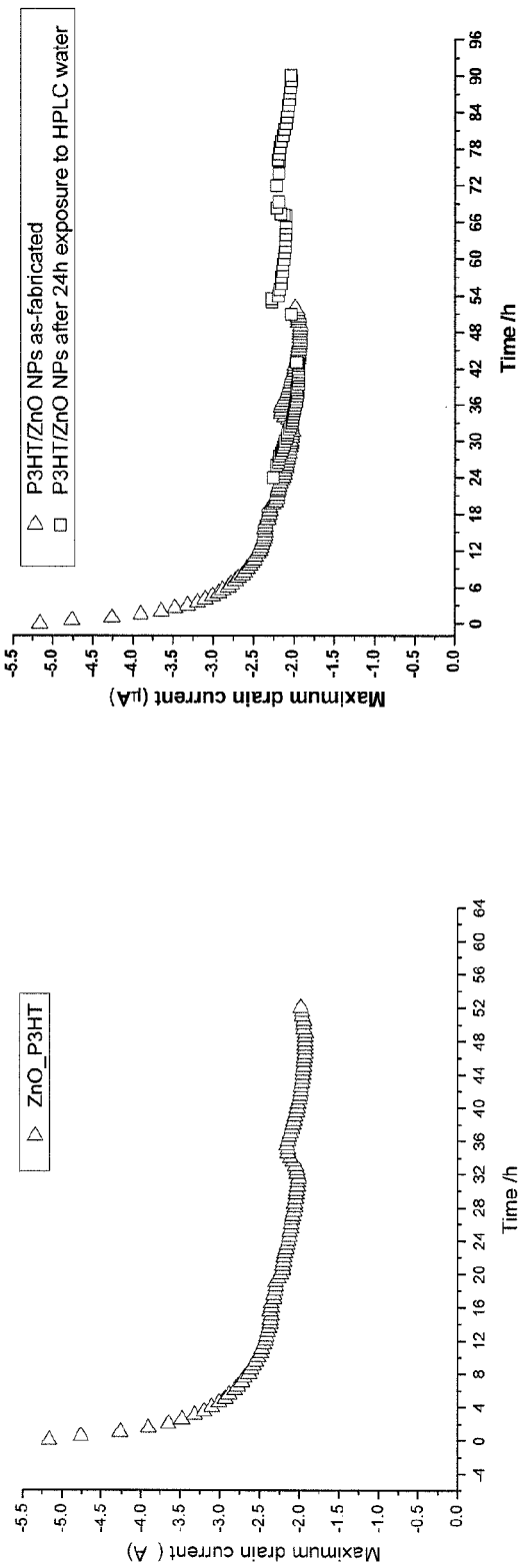

An example of the maximum drain current measured on a P3HT+ZnO-NP p-type semiconductor using the water-gated TFT structure 16 shown in FIG. 8 is provided in FIG. 10A. It is apparent that the stabilization of the P3HT+ZnO-NPs semiconductor occurs in about 12 hours, and it stays stable for 40 hours. The P3HT stabilization takes much longer. The overall output current measured is also generally higher with the nanocomposite semiconductor.

Alternatively, it has been observed that stable operation of the water-gated TFT can be obtained by exposing the P3HT+ZnO-NPs nanostructured channel to HPLC water for 24 h. A reproducible signal can be reached after this exposure time that is comparable to results obtained by applying the cycling protocol for the first 12 hours. After stabilization, the operation of gate electrode 24' cycled for the first 12 hours (hollow triangles) and just kept in water for the first 24 hours (hollow squares), both cycled afterwards over a period of three days, is presented in FIG. 10B.

After the semiconductor stabilization is accomplished with the water-gated TFT 16 the stable transfer curve is stored as reference channel current level, $I_0$. Owing to the fact that the electronic-reference gate 14' is kept fixed in its position it is always possible to control how stable the semiconductor stays during the measurement of the whole calibration curve that is carried out by biasing the sensing-gate 24'. In the array structure of the array device AD this can be done, also independently, for all the wells 20. Such a structure therefore enables, even in the cases in which the semiconductor is not stable enough, to continuously measure the current baseline value by using the reference-gate.

The sensing of the IgG and DNA strand as analyte or target molecules has been carried out on the water-gated TFT BS' shown in FIG. 8. The measurements have been carried in both phosphate buffer saline solution, diluted human saliva and whole bovine serum. At first, the bio-functionalization of gate 24' resulting in the deposition of the C_SAM and of the B_SAM formed either of the anti-IgG+ BSA or of the complementary strand of the target DNA was carried out. Only the 28 surface of the foot of the "L" shaped biosensing-gate was bio-functionalized as, during the process the other surface was covered. The covering layer was removed after the process was completed. Alternatively, both the surface can be covered by layer 30. As a further alternative the gate can be made out of a gold metallized polyimide layer.

Specifically, the C_SAM deposition procedure is the following: before functionalization, the gold surface was washed by immersion in boiling HPLC water for 10 min and UV/ozone cleaned for 10 min. The gold platelet was prior cleaned in a piranha solution ($H_2SO_4/H_2O_2$, 3:1 v/v) for 10 min, too. The C_SAM (Chem-SAM) on the gold surface comprises a layer of mixed alkanethiols terminating with carboxylic functionalities. To this end, a 10 mM solution consisting of 10:1 molar ratio of 3-MPA to 11-MUA was prepared in ethanol. The cleaned gold surface was immersed in the 3-MPA and 11-MUA solution and kept in the dark under constant $N_2$ flux for 18 h at 22° C.[1] The carboxylic groups are activated afterwards in a 200 mM EDC and 50 mM sulfo-NHS aqueous solution for 2 h at 25° C. This process is addressed in the text as EDC/sulfo-NHS chemical activation or simply as activation.

The IgG capturing SAM was generated, subsequently, through conjugation between the amine groups of the antibodies and the activated carboxylic groups on the gate surface, by immersing the gate in an anti-IgG phosphate buffer saline (PBS) solution for 2 h at 25° C. The solution was composed of 0.7 µM (0.1 mgml$^{-1}$) of anti-IgG and 10 mM (KCl 2.7 mM and 137 mM NaCl) of PBS at a pH of 7.4 and an ionic-strength ($i_s$) of 162 mM. Afterwards, to saturate the unreacted sulpho-NHS groups, the anti-IgG SAM was further treated with ethanolamine 1 M in PBS 10 mM for 1 h at 25° C. This latter step is addressed as the surface "chemical-blocking" or just blocking stage. Finally, the bio-functionalized gate was immersed in a 1.5 µM (0.1 mgml$^{-1}$) BSA solution in PBS 10 mM for 1 h at 25° C. This step of BSA physisorption is addressed as the "bio-blocking" of the gate surface. Both the conjugated anti-IgG and the adsorbed BSA form the herein addressed B_SAM). For the control experiment the B_SAM is formed by conjugating BSA (instead of anti-IgG), followed by the surface bio-blocking with BSA.

The DNA capturing layer was deposited according to the following protocol that starts from the EDC/sulfo-NHS chemically activated 3-MPA and 11-MUA (10:1) alkanethiols with terminating carboxylic groups. The gate surface with activated carboxylic groups was immersed in an Avidin (AV) phosphate buffer saline (PBS) solution for 2 h at 25° C. The solution was composed of 1.5 µM (0.1 mg/ml) of AV and 10 mM (KCl 2.7 mM and 137 mM NaCl) of PBS at pH 7.4 and $i_s$ 162 mM. Afterwards, to saturate the unreacted sulpho-NHS groups, the AV SAM was further treated with ethanolamine 1 M in PBS 10 mM for 1 h at 25° C. Finally, the gate was then immersed in a biotinylated single-strand DNA PBS solution 2 h at 25° C. The solution was composed of 0.5 µM of biotinylated single-strand DNA (sequence 5'-AGTGTGAGTTCTACCATTGCCAAA) and 10 mM (KCl 2.7 mM and 137 mM NaCl) of PBS at pH 7.4 and $i_s$ 162 mM.

After the bio-functionalization of the sensing-gate 24' with Human-anti-IgG, the Human-IgG bio-sensing was carried out according to the following protocol. The Human-anti-IgG bio-functionalized sensing-gate 24' is incubated (at RT and in the dark) for 10 min in 100 µl of PBS at pH of 7.4 and ionic-strength of 162 mM contained in a separate well. The gate is removed from the PBS solution, washed thoroughly with HPLC water, introduced into well of BS' as shown in FIG. 8 and a transfer characteristic (measured with the already described pulsed duty-cycle) is recorded, after a new stabilization cycling is performed. This latter process was carried out to stabilize the sensing-gate in the electric field and in the HPLC water environment. Afterwards, the same sensing-gate 24' is immersed and incubated (at RT and in the dark) for 10 min in 100 µl of the PBS standard-solutions of the IgG affinity ligands or in the IgM non affinity ligand with nominal concentrations ranging from $6 \cdot 10^{-2}$ zM ($10^{-21}$ M) to $6.67 \cdot 10^8$ zM. The evaluation of the error on the concentrations, or equivalently on the number of proteins sampled in 100 µl, was carried out considering both the Poisson and the dilution error. The total error at each concentration is computed as the square-root of the sum of the squares of the dilution and Poisson's uncertainties.

After incubation in each of the PBS standard-solutions of IgG or IgM starting from the more diluted one, the SAM 30 was washed thoroughly with HPLC water to remove the unreacted ligands away and a further I-V transfer curves were measured. Also in this case extra care was taken to positioning the gate always at the same height from the reference gate (ca. 4 mm) as for the measurement of the base-line in PBS, $I_0$. Also at this stage a stabilization of the current is carried out by measuring the transfer curve, in the forward and reverse run, until a few stable traces were recorded. Before the measurement of the $I_D$ current flowing in the transistor channel upon biasing with the sensing gate at each concentration, the same RU was gated also with the reference-gate 14' so as to always have an independent measure of the changes occurring in the RU that are independent from the sensing.

Figure 11:
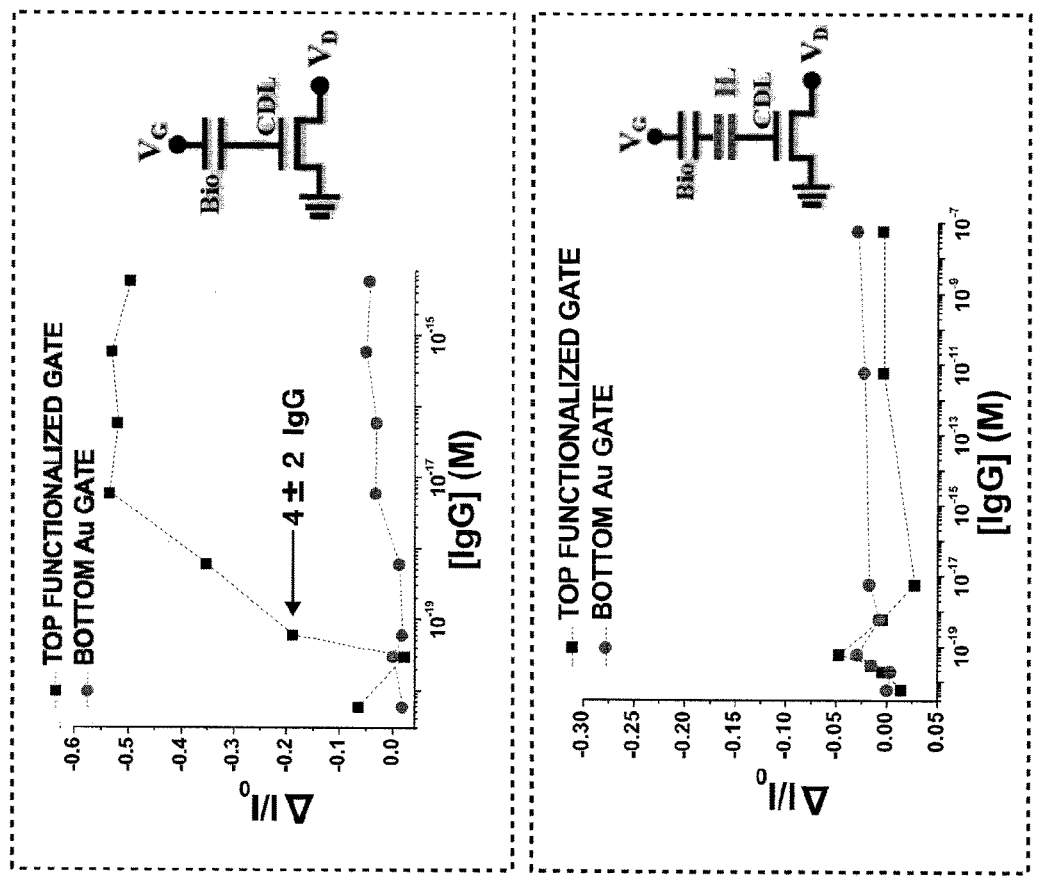
Figure 12:
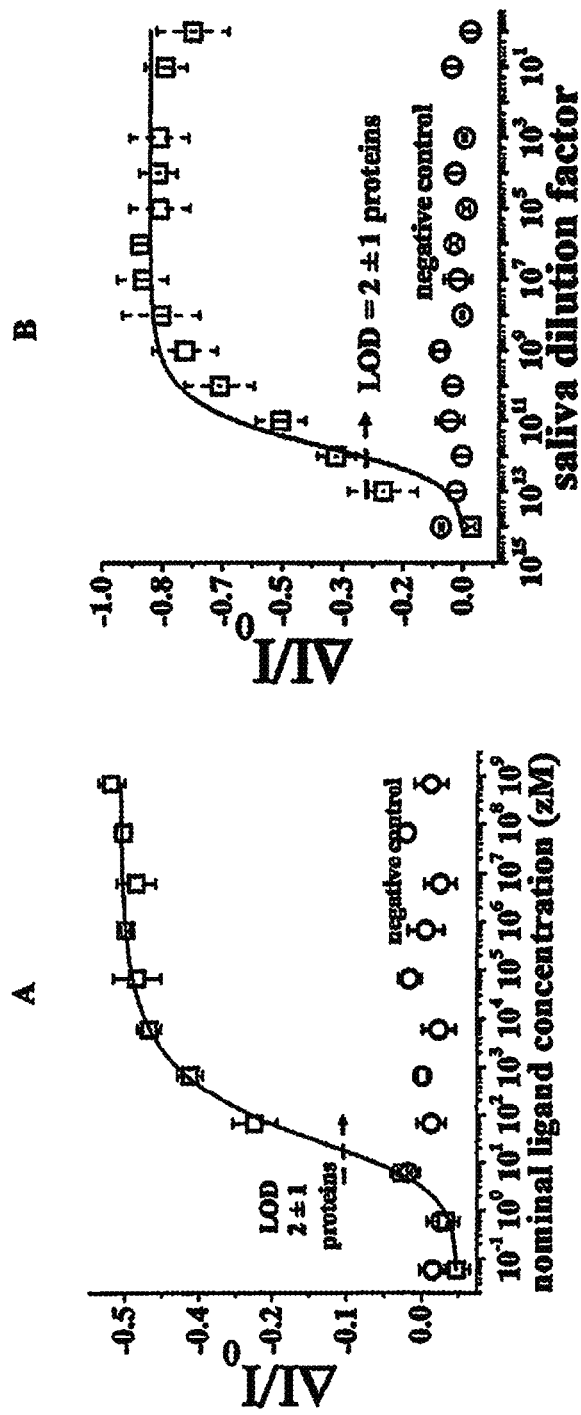

The stabilized currents measured after incubation in each standard solution are addressed as the "I" signal at a given concentration. The $\Delta I/I_0 = [(I-I_0)/I_0]$ is the normalized electronic response at a given concentration and the relevant dose-response or calibration curve is obtained by plotting these data at the $V_G$ value that maximizes the trans-conductance $\delta I_D/\delta V_G$ (falling generally in the −0.3 V to −0.4 V range), at all the investigated concentrations. One sole SAM functionalized gate (measured possibly also with the same P3HT or P3HT+ZnO-NPs channel 4) is used to measure a whole IgG or IgM dose-response-curve spanning eleven orders of magnitude ($6 \cdot 10^{-2}$ zM $−6.67 \cdot 10^8$ zM). The whole dose-curve for IgG is shown in FIG. 11 (top-panel) as full squares and it is also shown in FIG. 12A as hollow squares. In this case also the error bars over three replicates are provided. As it is apparent already at a concentration of 60 zM (4±2 IgG protein) a measurable 20% relative change in current is clearly observed. The circles are the relative current changes measured with the electronic-reference electrode 14' in FIG. 11 top panel. Indeed, the relative variation of the current measured on the reference gate, is much lower falling within 5-8%. This error level was used to validate the data set of one calibration curve as it proved that the current changes measured at extremely low ligand concentrations are due to the biochemical interactions and not to spurious effects such as the channel semiconductor material degradation. A negative control dose-curves involving the sensing of Human-IgM with a Human-anti-IgG layer 30 shown in FIG. 12A as hollow circles does not show an appreciable signal, demonstrating the specificity of the Human-anti-IgG interaction with the sole Human-IgG which is its affinity ligand.

The analysis of the dose curves of FIG. 11 (top-panel) invariably shows that a sizable change of $I_D$ is quantified at 60±30 zM, while the limit-of-detection (LOD) for $I_D$ is 20 zM. This means that a measurable signal is produced when as low as 2±1 IgG/anti-IgG complexes are formed over the ~$10^{12}$ anti-IgGs populating the gate surface. While in a control experiment, IgM is assayed showing no response. This proves that single-molecule detection is possible with this large millimetric size BS device here proposed. Further on, the detection is also selective.

Interesting is the experiment proposed in FIG. 11 (bottom-panel). Here a layer 0.4-0.5 mm thick of a solid ionic liquid, IL (agarose in this case), is deposited on the semiconductor channel area so as to generate a barrier between this layer 4 and the gating water 8. The equivalent circuit comprises not only the capacitance associated with the bio-layer ($C_{Bio}$) as well as that associated with the transistor channel ($C_{CDL}$) but also a third capacitance ($C_{IL}$) that is much smaller (because much thicker) than both the others. The agarose capacitance is therefore driving the gating of the TFT and, as it can be seen, the sensing of the IgG is completely switched off in this case. The sensing mechanisms can be explained by considering that in an electrolyte-gated TFT the capacitance associated with the bio-layer 30 on the gate 24 ($C_{Bio}$) is generally smaller compared to the capacitance associated with the charge-double-layer ($C_{CDL}$) at the semiconductor/water interface (Kim et al. Adv. Mater. Volume 25, Dec. 2, 2012, Pages 1822-1846, Mulla et al. Nat. Commun. Volume 6, Jan. 16, 2015 Pages 1-9, Manoli et al. Angewandte Chemie Volume 54, Issue 43, Oct. 19, 2015 Pages 12562-12576). Considering the simple but effective equivalent circuit shown in FIG. 11 (top-panel) it can be easily seen that the TFT is gated by the resultant of the two capacitance that are in series. So the TFT current is capacitive modulated by the bio-layer meaning that whatever happens in this layer is very sensitively transduced by the device. This is indeed the case also because pure water is used as electrolyte, no electrochemical-reference electrode is connected to the gate and the measurements are conducted in static or quasi-static setting. When a smaller capacitance is introduced that does not change with the bio-recognition event, the biosensing is turned off. The demonstrated extremely high sensitivity is inherent to the electronic amplification capabilities of the transistor-based electronic transduction. However, collective phenomena taking place in the biolayer of the highly packed recognition elements when the single binding event take place, play also a central role.

Human-IgG is assayed at the single-protein limit also in diluted human saliva with a Human-anti-IgG SAM. Data are shown in FIG. 12B. The sample of saliva was then diluted in PBS until no more IgG could be present. Saliva samples were collected by passive drool method from a healthy human female volunteer. The sampled saliva was divided into aliquots of 500 µl and frozen at −20° C. immediately after collection. When needed, a saliva aliquot was brought to room temperature, vortex and centrifuged at 1500× g for 15 minutes. As the sample of whole saliva was independently quantified by surface-plasmon resonance to comprise an endogenous IgG concentration of 40±6 nM, the collected supernatant was progressively diluted $1:10^{15}$ times in PBS. This was done to make sure that no endogenous IgG was present in the most diluted saliva solution.

For the assay, a single SAM gate was incubated for 10 min in each saliva solution, starting from the more diluted to more concentrated one, washed thoroughly in PBS and with HPLC water and measured with the transistor. As negative control experiment a gate functionalized with the sole BSA (both conjugated and adsorbed), was incubated in saliva solutions diluted in PBS. The data, averaged over three replicates, are displayed in FIG. 12B as red-squares. A SAM comprising no capturing anti-IgGs but only BSA, serves as negative control experiment to assess the selectivity of the assay platform in saliva as well as the noise level (FIG. 12B, black-circles). Eventually, no response was measured and the computed detection-limit in saliva is also, strikingly, down to a single IgG. The data points are relevant to three replicates for each dose-curve while the saliva was sampled from the same batch. The reproducibility error, over three replicates, is within 4% at most While the sensing mechanisms and its extraordinary electronic single-molecule sensitivity (e-SiMoA) will be exactly the same in the array device AD shown in FIG. 4, it is important to outline that the bio-functionalization of the gate 24 would be carried out slightly differently namely by pouring in the well 20 the needed solutions and by extensively washing when a given step is over and the solution is changed. Likewise, the dose curve would be measured by pouring in the well 20 the standard solutions and, after incubation, by washing and pouring water for the sensing measurement.

To prove that the technology proposed can also perform single-molecule detection in real samples, the sensing of IgG was also carried out in whole bovine serum, with the aforementioned biosensing protocol. It is to recall here that endogenous bovine-IgG found in bovine serum at the nM concentration level, will not selectively bind to the human anti-IgG attached to the gate 24'.

Figure 13:
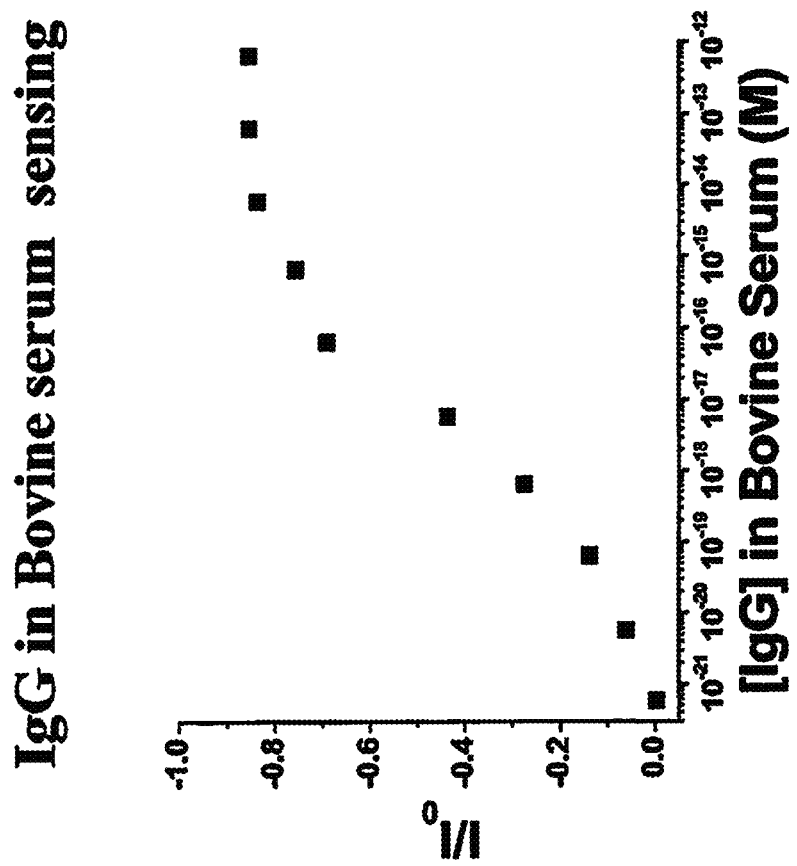

Also in this case the sensing was carried out by incubating, the sensing-gate 24' of BS' bio-functionalized with Human-anti-IgG capturing proteins, (at RT and in the dark) for 10 min in 100 µl of whole bovine serum. The gate is removed from the bovine serum, washed thoroughly with HPLC water, inserted into the HPLC water 8 of the BS' in FIG. 8. The TFT transfer characteristic is recorded, after the aforementioned stabilization trough cycling is performed. The same sensing-gate is then immersed and incubated (at RT and in the dark) for 10 min in 100 µl of bovine serum spiked with standard-aliquots of Human-IgG. The resulting nominal concentrations of the Human-IgG in the bovine serum ranged from $6 \cdot 10^{-2}$ zM ($10^{-21}$ M) to $6.67 \cdot 10^8$ zM. The whole dose-curve for Human-IgG spiked in bovine serum is shown in FIG. 13. The analysis of the dose curves shows that also in this case a sizable change of $I_D$ is measured already at 60 zM, proving the extremely high sensitivity of the proposed technology also in real samples.

The sensing of the DNA strand (sequence 5'-TTTGGCAATGGTAGAACTCACACT) in PBS has been carried out as well, after the bio-functionalization of gate 24' resulting in the attachment of the probe strand of DNA forming the layer 30 (sequence 5'-AGTGTGAGTTC-TACCATTGCCAAA). The DNA functionalization protocol was carried out as reported earlier on in the text.

Figure 14:
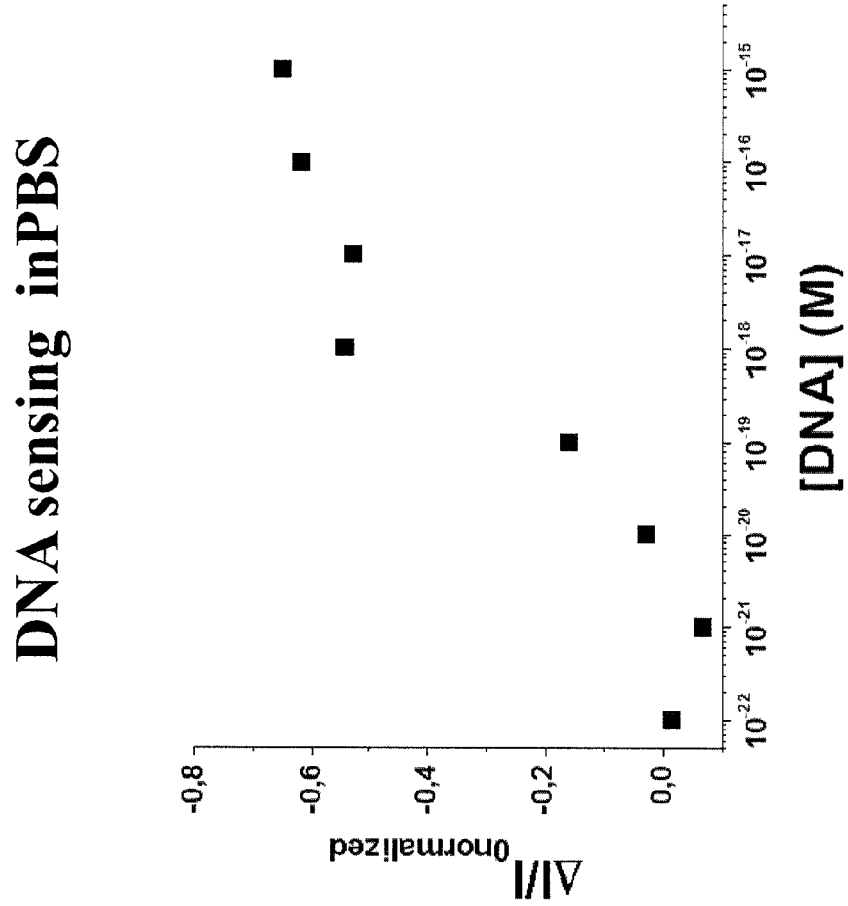

The bio-sensing protocol of the analyte or target DNA strand (complementary to the probe attached to the gate) is described in the following. The sensing gate 24' is incubated (at RT and in the dark) for 10 min in 100 µl of PBS at pH of 7.4 and ionic-strength of 162 mM. The gate is removed from the PBS solution, washed thoroughly with HPLC water, inserted into the well of BS'. The TFT transfer characteristic is recorded. The same sensing gate is immersed and incubated (at RT and in the dark) for 10 min in 100 µl of the PBS standard-solutions of the analyte sequence of the DNA strand with nominal concentrations ranging from $1 \cdot 10^{-2}$ zM ($10^{-21}$ M) to $10 \cdot 10^8$ zM in PBS. The whole dose-curve for DNA strand in PBS is shown in FIG. 14. The analysis of the dose curves shows that also in this case a sizable change of $I_D$ is measured at extremely low concentrations (100 zM).

Naturally, while the principle of the invention remains the same, the details of construction and the embodiments may widely vary with respect to what has been described and illustrated purely by way of example, without departing from the scope of the present invention.

The invention claimed is:

1. A field effect transistor (BS, BS') sensor including:
   a source-drain channel (2),
   a semiconductor layer (4) on said source-drain channel (2),
   a first gate electrode (14, 14') arranged above said semiconductor layer (4),
   a first well (6) enclosing said source-drain channel (2), said semiconductor layer (4) and said first gate electrode (14, 14'), the first well (6) being configured to be filled, in use, with a first liquid (8),
   a second well (20) configured to be filled, in use, with a second liquid (23), the second well (20) being arranged above the first well (6), and
   a second gate electrode (24, 24') arranged above the first gate electrode (14, 14') and exposed to an interior of the first well (6),
   wherein the second gate electrode (24, 24') provides at least a portion of a bottom wall of the second well (20).

2. The field effect transistor (BS, BS') of claim 1, wherein the second gate electrode (24, 24') is a sensing gate electrode and includes a first face (28) carrying a layer of biological recognition elements (30) including one or more specific-binding-pair-forming substances, and a second face (26) exposed to the interior of the first well (6).

3. The field effect transistor (BS, BS') of claim 2, wherein said first face (28) covered and second face (26) are opposite and equipotential.

4. The field effect transistor (BS, BS') of claim 3, wherein the second gate electrode (24, 24') includes a precursor (24P) coated with a layer of electrically conductive material, which is continuous across said opposite first and second faces (26, 28), thereby being equipotential on said opposite first and second faces (26, 28).

5. The field effect transistor (14; 14') of claim 1, wherein the first gate electrode (14; 14') is an electronic reference gate electrode.

6. The field effect transistor (BS, BS') of claim 1, including a substrate (12) carrying said source-drain channel (2), said substrate (12) laying at a bottom (10) of the first well (6).

7. The field effect transistor (BS, BS') of claim 1, including a substrate (12) carrying said source-drain channel, said substrate (12) being provided by a bottom (10) of the first well (6).

8. The field effect transistor sensor (BS, BS') of claim 1, wherein the first well (6) includes a plurality of pillars (18) supporting the second well (20).

9. The field effect transistor sensor (BS, BS') of claim 1, wherein a rim on side walls of the first well (6) supports the second well (20).

10. The field effect transistor sensor of claim 1, wherein said second gate electrode (24, 24') includes a core substrate (KS), and a first layer (GL1) and a second layer (GL2) of electrically conductive material, coating opposite faces of said core substrate (KS), said first and second layers of electrically conductive material being equipotential via a conductive bridge extending through said core substrate (KS).

11. The field effect transistor sensor (BS, BS') of claim 1, wherein the second gate electrode (24, 24') includes first and second faces (A, B, C, D, E) on opposite sides of a circuit board (BRD) with electrical connections departing from each of the first and second faces and ending at corresponding locations on said opposite sides of the circuit board (BRD).

12. The field effect transistor sensor (BS, BS') of claim 1, wherein said semiconductor layer comprises a P3HT+ZnO-NP p-type semiconductor.

13. The field effect transistor sensor (BS, BS') of claim 1, wherein the first gate electrode (14, 14') is spaced from the semiconductor layer (4).

14. The field effect transistor sensor (BS, BS') of claim 1, wherein the second gate electrode (24; 24') is spaced from the first gate electrode (14; 14').

15. An array device (AD, AD') including an array of field effect transistor sensors (BS, BS') according to claim 1.

16. The array device (AD, AD') of claim 15, including a lower plate (60) defining a first volume, a bottom of said first volume comprising a pattern of resistor units (RU), each resistor unit including said source-drain channel (2) and said semiconductor layer (4), said first volume providing the first well (6) for said pattern of resistor units (RU).

17. The array device (AD) of claim 16, including an upper plate (200) provided with a corresponding pattern of receptacles defining the second wells (20) for corresponding resistor units (RU), a bottom of each receptacle being provided by a corresponding second gate electrode (24) located above one or more corresponding first gate electrodes (14') housed in the lower plate (60), the upper plate (200) being stacked onto said lower plate (60).

18. The array device (AD') of claim 16, including an upper plate (200') having a framework-like structure with bridging members (B24) extending across the framework-like structure, said bridging members supporting a pattern of said second gate electrodes (24') above one or more corresponding first gate electrodes (14') housed in the lower plate (60), the upper plate (200) being stacked onto said lower plate (60).

* * * * *